US006599312B2

(12) United States Patent
Dobak, III

(10) Patent No.: US 6,599,312 B2
(45) Date of Patent: Jul. 29, 2003

(54) ISOLATED SELECTIVE ORGAN COOLING APPARATUS

(75) Inventor: John D. Dobak, III, La Jolla, CA (US)

(73) Assignee: Innercool Therapies, Inc., San Diego, CA (US)

(*) Notice: Subject to any disclaimer, the term of this patent is extended or adjusted under 35 U.S.C. 154(b) by 0 days.

(21) Appl. No.: 09/871,145

(22) Filed: May 29, 2001

(65) Prior Publication Data
US 2002/0002394 A1 Jan. 3, 2002

Related U.S. Application Data

(63) Continuation of application No. 09/292,532, filed on Apr. 15, 1999, which is a continuation-in-part of application No. 09/103,342, filed on Jun. 23, 1998, now Pat. No. 6,096,068, and a continuation-in-part of application No. 09/047,012, filed on Mar. 24, 1998, now Pat. No. 5,957,963, and a continuation-in-part of application No. 09/052,545, filed on Mar. 31, 1998, now Pat. No. 6,231,595.

(51) Int. Cl.⁷ .................................................. A61F 7/00

(52) U.S. Cl. .......................... 607/105; 607/106; 607/98

(58) Field of Search ........................ 607/96, 104, 105, 607/106, 108, 109, 113

(56) References Cited

U.S. PATENT DOCUMENTS

| 2,308,484 A | 1/1943 | Auzin et al. |
| 2,374,609 A | 4/1945 | McCollum |
| 2,615,686 A | 10/1952 | Davidson |
| 2,672,032 A | 3/1954 | Towse |
| 2,913,009 A | 11/1959 | Kuthe |
| 3,125,096 A | 3/1964 | Antiles, et al. |
| 3,298,371 A | 1/1967 | Lee |

(List continued on next page.)

FOREIGN PATENT DOCUMENTS

| EP | 0655225 A1 | 5/1993 |
| FR | 2 447 406 | 3/1980 |
| GB | 0 664 990 | 11/1997 |
| SU | 806 029 | 2/1981 |
| WO | 91/05528 | 5/1991 |
| WO | 93/04727 | 3/1993 |
| WO | 95/01814 | 1/1995 |

(List continued on next page.)

OTHER PUBLICATIONS

Duklunder, G.M., et al.; "Influence of Ventilation of the Face on Thermoregulation in Man During Hyper- and Hypothermia"; Eur. J. Appl. Physiol; 62;342–348 (1991).
Maas, C., et al.; "Intermittent Antegrade/Selective Cerebral Perfusion During Circulatory Arrest for Repair of the Aortic Arch"; Perfusion; vol. 12; pp. 127–132 (1997).
Gerbrandy, et al.; "Oral, Rectal and Esophageal Temperatures in Relation to Central Temperature Control in Man"; Clin Sci (Colch); 13:615–624 (1954).
Ambrus; *The Biphasic Nature and Temperature Dependence of the Activation of Human Plasminogen by Urokinase*; May 1979; pp. 339–347; Research Communications in Chemical Pathology and Pharmacology, vol. 24, No. 2.
Bigelo; *Hypothermia, Its Possible Role in Cardiac Surgery*; Nov. 1959; pp. 849–866; Annals of Surgery, vol. 132, No. 5.
Cheatle; *Cryostripping the Long and Short Saphenous Veins*; Jan. 1993; one page; Br. J. Surg., vol. 80.

(List continued on next page.)

Primary Examiner—Roy Gibson
(74) Attorney, Agent, or Firm—Gerald W. Spinks

(57) ABSTRACT

A selective organ cooling device with a separate warming device for preventing secondary cooling which can result from cooling the selected organ. The cooling device applies cooling to the blood flowing in the feeder artery of the selected organ, while the body temperature control device warms the whole body either directly, or by warming blood returning to the heart from the selected organ, via a vein.

10 Claims, 9 Drawing Sheets

U.S. PATENT DOCUMENTS

| | | |
|---|---|---|
| 3,425,419 A | 2/1969 | Dato |
| 3,504,674 A | 4/1970 | Swenson et. al. |
| 3,612,175 A | 10/1971 | Ford et al. |
| 3,839,621 A * | 10/1974 | Hariu .................... 222/153.13 |
| 3,865,116 A | 2/1975 | Brooks |
| 3,888,259 A | 6/1975 | Miley |
| 3,971,383 A | 7/1976 | Van Gerven |
| 4,038,519 A | 7/1977 | Foucras |
| 4,149,541 A * | 4/1979 | Gammons et al. .......... 607/104 |
| 4,153,048 A | 5/1979 | Magrini |
| 4,190,033 A | 2/1980 | Foti |
| 4,231,425 A | 11/1980 | Engstrom |
| 4,275,734 A | 6/1981 | Mitchiner |
| 4,298,006 A | 11/1981 | Parks |
| 4,318,722 A | 3/1982 | Altman |
| 4,323,071 A | 4/1982 | Simpson et al. |
| 4,427,009 A | 1/1984 | Wells et al. |
| 4,445,500 A | 5/1984 | Osterholm |
| 4,483,341 A | 11/1984 | Witteles |
| 4,502,286 A | 3/1985 | Okada et al. |
| 4,569,355 A | 2/1986 | Bitterly |
| 4,581,017 A | 4/1986 | Sahota |
| 4,602,642 A | 7/1986 | O'Hara et al. |
| 4,655,746 A | 4/1987 | Daniels et al. |
| 4,672,962 A | 6/1987 | Hershenson |
| 4,745,922 A | 5/1988 | Taylor |
| 4,748,979 A | 6/1988 | Hershenson |
| 4,750,493 A | 6/1988 | Brader |
| 4,762,129 A | 8/1988 | Bonzel |
| 4,762,130 A | 8/1988 | Fogarty et al. |
| 4,781,799 A | 11/1988 | Herbert, Jr. et al. |
| 4,820,349 A | 4/1989 | Saab |
| 4,860,744 A | 8/1989 | Johnson et al. |
| 4,883,455 A | 11/1989 | Leonard |
| 4,894,164 A | 1/1990 | Polaschegg |
| 4,904,237 A | 2/1990 | Janese |
| 4,920,963 A | 5/1990 | Brader |
| 4,951,677 A | 8/1990 | Crowley et al. |
| 4,964,409 A | 10/1990 | Tremulis |
| 5,000,734 A | 3/1991 | Boussignac et al. |
| 5,002,531 A | 3/1991 | Bonzel |
| 5,014,695 A | 5/1991 | Benak et al. |
| 5,018,521 A | 5/1991 | Campbell |
| 5,019,075 A | 5/1991 | Spears et al. |
| 5,024,668 A | 6/1991 | Peters et al. |
| 5,041,089 A | 8/1991 | Mueller et al. |
| 5,046,497 A | 9/1991 | Millar |
| 5,078,713 A | 1/1992 | Varney |
| 5,089,260 A | 2/1992 | Hunter et al. |
| 5,092,841 A | 3/1992 | Spears |
| 5,106,360 A | 4/1992 | Ishiwara et al. |
| 5,108,390 A | 4/1992 | Potocky et al. |
| 5,110,721 A | 5/1992 | Anaise et al. |
| 5,112,438 A | 5/1992 | Bowers |
| 5,117,822 A | 6/1992 | Laghi |
| 5,147,355 A | 9/1992 | Friedman et al. |
| 5,149,321 A | 9/1992 | Klatz et al. |
| 5,150,706 A | 9/1992 | Cox et al. |
| 5,151,100 A | 9/1992 | Abele et al. |
| 5,180,364 A | 1/1993 | Ginsburg |
| 5,190,539 A | 3/1993 | Fletcher et al. |
| 5,191,883 A | 3/1993 | Lennox et al. |
| 5,196,024 A | 3/1993 | Barath |
| 5,211,631 A | 5/1993 | Sheaff |
| 5,234,405 A | 8/1993 | Klatz et al. |
| 5,248,312 A | 9/1993 | Langberg |
| 5,250,070 A | 10/1993 | Parodi |
| 5,257,977 A | 11/1993 | Eshel |
| 5,264,260 A | 11/1993 | Saab |
| 5,267,341 A | 11/1993 | Shearin |
| 5,269,369 A | 12/1993 | Faghri |
| 5,269,749 A | 12/1993 | Koturov |
| 5,269,758 A | 12/1993 | Taheri |
| 5,281,213 A | 1/1994 | Milder et al. |
| 5,281,215 A | 1/1994 | Milder |
| 5,295,949 A * | 3/1994 | Hathaway .................... 482/10 |
| 5,306,261 A | 4/1994 | Alliger et al. |
| 5,310,440 A | 5/1994 | Zingher |
| 5,334,193 A | 8/1994 | Nardella |
| 5,342,301 A | 8/1994 | Saab |
| 5,344,436 A | 9/1994 | Fontenot et al. |
| 5,365,750 A | 11/1994 | Greenthal |
| 5,368,591 A | 11/1994 | Lennox et al. |
| 5,383,854 A | 1/1995 | Safar et al. |
| 5,383,918 A | 1/1995 | Panetta |
| 5,395,314 A | 3/1995 | Klatz et al. |
| 5,395,331 A | 3/1995 | O'Neill, et al. |
| 5,403,281 A | 4/1995 | O'Neill, et al. |
| 5,417,686 A | 5/1995 | Peterson et al. |
| 5,423,745 A | 6/1995 | Todd et al. |
| 5,423,807 A | 6/1995 | Milder |
| 5,433,740 A | 7/1995 | Yamaguchi |
| 5,437,673 A | 8/1995 | Baust et al. |
| 5,443,456 A | 8/1995 | Alliger et al. |
| 5,462,521 A | 10/1995 | Brucker et al. |
| 5,486,204 A | 1/1996 | Clifton |
| 5,486,208 A | 1/1996 | Ginsburg |
| 5,496,271 A | 3/1996 | Burton et al. |
| 5,531,776 A | 7/1996 | Ward et al. |
| 5,549,559 A | 8/1996 | Eshel |
| 5,554,119 A | 9/1996 | Harrison et al. |
| 5,558,644 A | 9/1996 | Boyd et al. |
| 5,573,532 A | 11/1996 | Chang et al. |
| 5,578,008 A | 11/1996 | Hara |
| 5,584,804 A | 12/1996 | Klatz et al. |
| 5,588,438 A | 12/1996 | McKown et al. |
| 5,591,162 A | 1/1997 | Fletcher et al. |
| 5,620,480 A | 4/1997 | Rudie |
| 5,622,182 A | 4/1997 | Jaffe |
| 5,624,392 A | 4/1997 | Saab |
| 5,630,837 A | 5/1997 | Crowley |
| 5,643,197 A | 7/1997 | Brucker et al. |
| 5,643,336 A * | 7/1997 | Lopez-Claros .............. 607/104 |
| 5,647,051 A | 7/1997 | Neer |
| 5,653,692 A | 8/1997 | Masterson et al. |
| 5,709,654 A | 1/1998 | Klatz et al. |
| 5,713,941 A | 2/1998 | Robins et al. |
| 5,716,386 A | 2/1998 | Ward et al. |
| 5,733,318 A | 3/1998 | Augustine |
| 5,735,809 A | 4/1998 | Gorsuch |
| 5,797,878 A | 8/1998 | Bleam |
| 5,799,661 A | 9/1998 | Boyd et al. |
| 5,800,480 A | 9/1998 | Augustine et al. |
| 5,800,483 A | 9/1998 | Vought |
| 5,800,516 A | 9/1998 | Fine et al. |
| 5,807,391 A | 9/1998 | Wijkamp |
| 5,820,593 A | 10/1998 | Safar et al. |
| 5,824,030 A | 10/1998 | Yang et al. |
| 5,827,222 A | 10/1998 | Klatz et al. |
| 5,827,237 A | 10/1998 | Macoviak et al. |
| 5,827,269 A | 10/1998 | Saadat |
| 5,833,671 A | 11/1998 | Macoviak et al. |
| 5,837,003 A | 11/1998 | Ginsburg |
| 5,861,021 A | 1/1999 | Thome et al. |
| 5,868,735 A | 2/1999 | Lafontaine |
| 5,871,526 A | 2/1999 | Gibbs et al. |
| 5,873,835 A | 2/1999 | Hastings et al. |
| 5,879,316 A | 3/1999 | Safar et al. |
| 5,879,329 A | 3/1999 | Ginsburg |
| 5,899,898 A | 5/1999 | Arless et al. |
| 5,899,899 A | 5/1999 | Arless et al. |

| | | |
|---|---|---|
| 5,902,268 A | 5/1999 | Saab |
| 5,906,588 A | 5/1999 | Safar et al. |
| 5,906,594 A | 5/1999 | Scarfone et al. |
| 5,906,636 A | 5/1999 | Casscells, III et al. |
| 5,913,856 A | 6/1999 | Chia et al. |
| 5,913,885 A | 6/1999 | Klatz et al. |
| 5,913,886 A | 6/1999 | Soloman |
| 5,916,242 A | 6/1999 | Schwartz |
| 5,957,963 A | 9/1999 | Dobak, III |
| 5,964,751 A | 10/1999 | Amplatz et al. |
| 5,971,979 A | 10/1999 | Joye et al. |
| 5,989,238 A | 11/1999 | Ginsburg |
| 6,007,692 A | 12/1999 | Herbert et al. |
| 6,019,783 A | 2/2000 | Philips et al. |
| 6,022,336 A | 2/2000 | Zadno-Azizi et al. |
| 6,024,740 A | 2/2000 | Lesh et al. |
| 6,033,383 A | 3/2000 | Ginsburg |
| 6,042,559 A | 3/2000 | Dobak, III |
| 6,051,019 A | 4/2000 | Dobak, III |
| 6,063,101 A | 5/2000 | Jacobsen et al. |
| 6,096,068 A | 8/2000 | Dobak, III et al. |
| 6,110,168 A | 8/2000 | Ginsburg |
| 6,126,684 A | 10/2000 | Gobin et al. |
| 6,146,411 A | 11/2000 | Noda et al. |
| 6,146,814 A | 11/2000 | Millet |
| 6,149,670 A | 11/2000 | Worthen et al. |
| 6,149,673 A | 11/2000 | Ginsburg |
| 6,149,676 A | 11/2000 | Ginsburg |
| 6,149,677 A | 11/2000 | Dobak, III |
| 6,165,207 A | 12/2000 | Balding et al. |
| 6,224,624 B1 | 5/2001 | Lasheras et al. |
| 6,231,595 B1 | 5/2001 | Dobak, III |
| 6,235,048 B1 | 5/2001 | Dobak, III |
| 6,238,428 B1 | 5/2001 | Werneth et al. |
| 6,245,095 B1 | 6/2001 | Dobak, III et al. |
| 6,251,129 B1 | 6/2001 | Dobak, III et al. |
| 6,251,130 B1 | 6/2001 | Dobak, III et al. |
| 6,254,626 B1 | 7/2001 | Dobak, III et al. |
| 6,261,312 B1 | 7/2001 | Dobak, III et al. |
| 6,264,679 B1 | 7/2001 | Keller et al. |
| 6,290,697 B1 | 9/2001 | Tu et al. |
| 6,290,717 B1 | 9/2001 | Philips |
| 6,295,990 B1 | 10/2001 | Lewis et al. |
| 6,303,156 B1 | 10/2001 | Ferrigno |
| 6,306,161 B1 | 10/2001 | Ginsburg |
| 6,312,452 B1 | 11/2001 | Dobak, III et al. |
| 6,312,453 B1 | 11/2001 | Stefanile et al. |
| 6,338,727 B1 | 1/2002 | Noda et al. |
| 6,364,899 B1 | 4/2002 | Dobak, III |
| 6,368,304 B1 | 4/2002 | Aliberto et al. |
| 6,375,673 B1 | 4/2002 | Clifton et al. |
| 6,379,378 B1 | 4/2002 | Werneth et al. |
| 2001/0001830 A1 | 5/2001 | Dobak, III et al. |
| 2001/0001831 A1 | 5/2001 | Dobak, III et al. |
| 2001/0001832 A1 | 5/2001 | Dobak, III et al. |
| 2001/0002442 A1 | 5/2001 | Dobak, III |
| 2001/0005791 A1 * | 6/2001 | Ginsburg et al. ........... 607/106 |
| 2001/0007951 A1 | 7/2001 | Dobak, III |
| 2001/0008975 A1 | 7/2001 | Dobak, III et al. |
| 2001/0010011 A1 | 7/2001 | Aliberto et al. |
| 2001/0016764 A1 | 8/2001 | Dobak, III |
| 2001/0021865 A1 | 9/2001 | Dobak, III et al. |
| 2001/0021866 A1 | 9/2001 | Dobak, III et al. |
| 2001/0029394 A1 | 10/2001 | Dobak, III et al. |
| 2001/0031946 A1 | 10/2001 | Walker et al. |
| 2001/0041923 A1 | 11/2001 | Dobak, III |
| 2001/0047191 A1 | 11/2001 | Lasersohn et al. |
| 2001/0047192 A1 | 11/2001 | Lasersohn et al. |
| 2001/0047196 A1 | 11/2001 | Ginsburg et al. |
| 2001/0049545 A1 | 12/2001 | Lasersohn et al. |
| 2002/0002394 A1 | 1/2002 | Dobak, III |
| 2002/0007179 A1 | 1/2002 | Dobak, III et al. |
| 2002/0007202 A1 | 1/2002 | Dobak, III et al. |
| 2002/0007203 A1 | 1/2002 | Gilmartin et al. |
| 2002/0026227 A1 | 2/2002 | Philips |
| 2002/0029016 A1 | 3/2002 | Pham et al. |
| 2002/0032430 A1 | 3/2002 | Luo et al. |
| 2002/0032474 A1 | 3/2002 | Dobak, III et al. |
| 2002/0040717 A1 | 4/2002 | Dobak, III |
| 2002/0045852 A1 | 4/2002 | Saab |
| 2002/0045924 A1 | 4/2002 | Fox |
| 2002/0045925 A1 | 4/2002 | Keller et al. |
| 2002/2004589 | 4/2002 | Kramer |

FOREIGN PATENT DOCUMENTS

| | | |
|---|---|---|
| WO | 96/40347 | 12/1996 |
| WO | WO 97/01374 | 1/1997 |
| WO | WO 97/25011 | 7/1997 |
| WO | WO 98/26831 | 6/1998 |
| WO | WO 98/31312 | 7/1998 |
| WO | WO 99/37226 | 7/1999 |
| WO | WO 99/48449 | 9/1999 |
| WO | WO 99/66970 | 12/1999 |
| WO | WO 99/66971 | 12/1999 |
| WO | WO 00/09054 | 2/2000 |
| WO | WO 00/10494 | 3/2000 |
| WO | WO 00/38601 | 7/2000 |
| WO | WO 00/47145 | 8/2000 |
| WO | WO 00/48670 | 8/2000 |
| WO | WO 00/51534 | 9/2000 |
| WO | WO 00/53135 | 9/2000 |
| WO | WO 00/57823 | 10/2000 |
| WO | WO 00/62837 | 10/2000 |
| WO | WO 00/66053 | 11/2000 |
| WO | WO 00/72779 | 12/2000 |
| WO | WO 00/72787 | 12/2000 |
| WO | WO 01/03606 | 1/2001 |
| WO | WO 01/08580 | 2/2001 |
| WO | WO 01/10323 | 2/2001 |
| WO | WO 01/10365 | 2/2001 |

OTHER PUBLICATIONS

Colvett, K. T., A. F. Althausen, B. Bassil, N. M. Heney, F. V. McGovern, H. H. Youn, D. S. Kaufman, A. L. Zietman, and W. U. Shipley, *Opportunities with Combined Modality Therapy for Selective Organ Preservation in Muscle–Invasive Bladder Cancer*, 1996, pp. 201–208, Journ. of Surg. Oncology, vol. 63.

Dexter; *Blood Warms as It Blows Retrograde from a Femoral Cannulation Site to the Carotid Artery During Cardiopulmonary Bypass*; Nov. 1994; pp. 393–397; Perfusion, vol. 9, No. 6.

Gillinov; *Superior Cerebral Protection with Profound Hypothermia During Circulatory Arrest*; Nov. 1992; pp. 1432–1439; Ann. Thorac. Surg., vol. 55.

Higazi; *The Effect of Ultrasonic Irradiation and Temperature on Fibrinolytic Activity in Vitro*; Aug. 1992; pp.251–253; Thrombosis Research, vol. 69, No. 2.

Iaizzo, *Facial Warming Increases the Threshold for Shivering*, 1999; pp. 231–239, Journ. of Neurosurgical Anesthesiology, vol. 11, No. 4.

Imamaki; *Retrograde Cerebral Perfusion with Hypothermic Blood Provides Efficient Protection of the Brain*; Jul. 1995; pp. 325–333; Journal of Cardiac Surgery, vol. 10, No. 4, Part 1.

Jolin; *Management of a Giant Intracranial Aneurysm Using Surface–Heparinized Extracorporeal Circulation and Controlled Deep Hypothermic Low Flow Perfusion*; Aug. 1992; pp. 756–760; Acta Anaesthesiologica Scandinavia.

Jos R.C. Jansen, Ph.D., et al. (1997) *Near Continuous Cardiac Output by Thermodilution*. Journal of Clinical Monitoring 13:233–239.

Kimoto; *Open Heart Surgery under Direct Vision with the Aid of Brain–Cooling by Irrigation*; Jul. 1955; pp. 592–603; Surgery, vol. 39, No. 4.

Marekovic, Z.; *Abstract of Renal Hypothermia in Situ by Venous Passages*: Experimental Work on Dogs; 1980; Eur Urol 6(2); 1 page.

Mass, C., Kok, P. Segers, A. Boogaart, S. Eilander, I. de Vries, *Intermittent Antegrade/Selective Cerebral Perfusion during Circulatory Arrest for Repair of the Aortic Arch*, 1997, pp. 127–132, Perfusion, vol. 12.

Meden; *Effect of Hypothermia and Delayed Thrombolysis in a Rat Embolic Stroke Model*; Dec. 1993; pp. 91–98; Acta Neurologica Scandinavica.

Meden; *The Influence of Body Temperature on Infarct Volume and Thrombolytic Therapy in a Rat Embolic Stroke Model*; Feb. 1994; pp. 131–138; Brain Research, Vol. 647.

Milleret, Rene; *La cryo–chirurgie danes les varices des mimbres inferieurs*; Anglologie; Supplement au No. 110.

Milleret; Abstract of *Cryosclerosis of the Saphenous Veins in Varicose Reflux in the Obese and Elderly*; 10.1981; one page; Phlebologie, vol. 34, No. 4.

Parkins; *Brain Cooling in the Prevention of Brain Damage During Periods of Circulatory Occlusion in Dogs*; Apr. 1954; pp. 284–289; Annals of Surgery, vol. 140, No. 3.

Piepgras; *Rapid Active Internal Core Cooling for Induction of Moderate Hypothermia in Head Injury by Use of an Extracorporeal Heat Exchanger*; Feb. 1998; pp. 311–318; Neurosurgery, vol. 42, No. 2.

Rijken; *Plasminogen Activation at Low Temperatures in Plasma Samples Containing Therapeutic Concentrations of Tissue–Type Plasminogen Activator or Other Thrombolytic Agents*; Oct. 1989; pp. 47–52; place of publication unknown.

Schwartz, A.E. et al.; (1996); *Isolated cerebral hypothermia by single carotid artery perfusion of extracorporeally cooled blood in baboons*; Neurosurgery 39(3):577–582.

Schwartz; *Cerebral Blood Flow during Low–flow Hypothermic Cardiopulmonary Bypass in Baboons*; Jun. 1994; pp. 959–964; Anesthesiology, vol. 81, No. 4.

Schwartz, *Selective Cerebral Hypothermia by Means of Transfemoral Internal Carotid Artery Catheterization*; May 1996; pp. 571–572; Radiology, Vol. 201, No. 2.

Steen; *The Detrimental Effects of Prolonged Hypothermia and Rewarming in the Dog*; Aug. 1979;pp. 224–230; Anesthesiology, vol. 52, No. 3.

Vandam; *Hypothermia*; Sep. 1959; pp. 546–553; The New England Journal of Medicine.

White; *Cerebral Hypothermia and Circulatory Arrest*; Jul. 1978; pp. 450–458; Mayo Clinic Proceedings, vol. 53.

Yenari, *Thrombolysis with Tissue Plasminogen Activator (TPA) is Temperature Dependent*; Jul. 1994; pp. 475–481; Thrombosis Research, vol. 77, No. 5.

Yoshihara; *Changes in Coagulation and Fibrinolysis Occurring in Dogs during Hypothermia*; Aug. 1984; pp. 503–512; Thrombosis Research, vol. 37, No. 4.

Zarins; *Circulation in Profound Hypothermia*; Nov. 1972; pp. 97–104; Journal of Surgical Research, vol. 14, No. 2.

Alfonsi, P., D. I. Sessler, B. Du Manior, J–C Levron, J–P. Le Moing, M. Chauvin, "The Effects of Meperidine and Sufentanil on the Shivering Threshold in Postoperative Patients," *Anesthesiology*, 89(1):43–48, Jul. 1998.

Cabanac, M.; "Selective brain cooling and thermoregulatory set–point"; Journal of Basic & Clinical Physiology & Pharmacology; Department de Physiologie, Faculte de medecine, Universite Laval, Quebec QC, Canada G1K 7P4; Freund Publishing House Ltd., 1998; pp. 3–13.

Capogna, G., et al.; "IV Clonidine for Post–Extradural Shivering in parturients: a Preliminary Study"; *British Journal of Anaesthesia*; 71:294–295, 1993.

Cheng, C. et al. (1995), "Increasing Mean Skin Temperature Linearly Reduces the Core–Temperature Thresholds for Vasoconstriction and Shivering in Humans," *Anesthesiology* 82(5):1160–1168, May.

Deklunder, G., M. Dauzat, J–L. Lecroart, J–J. Hauser, and Y. Houdas, "Influence of Ventilation of the Face on Thermoregulation in Man during Hyper–and Hypothermia," *Eur. J. Appl. Physiol.*, 1991, 62:342–348.

Gentilello, L.M., "Advances in the Management of Hypothermia," *Horizons in Trauma Surgery*, 75(2):243–256, Apr. 1995.

Giuffre, M. et al. (1991), "Rewarming Postoperative Patients: Lights, Blankets, or Forced Warm Air," *Journal of Post Anesthesia Nursing*, 6(6):386–393, Dec.

Guffin, Anita, et al.; "Shivering Following Cardiac Surgery: Hemodynamic Changes and Reversal."; *Journal of Cardiothoracic Anesthesia*, 1(1).24–28, Feb. 1987.

Haley, E. C. et al. "A Randomized Trial of Tirilazad Mesylate in Patients with Acute Stroke (RANTTAS)," *Stroke*, 27(9):1453–1458, 1996.

Keegan, M. T. et al. "Shivering Complicating the Treatment of Neurologically Impaired Surgical and Intensive Care Unit Patients," *Anesthesiology*, 91(3):874–876, Sep. 1999.

Kurz, Martin, et al.; "Naloxone, Meperidine, and Shivering, "; *Anesthesiology*; 79(6);1193–1201; Dec. 1983.

Lennon, Robert L. et al. "Evaluation of a Force–Air for Warming Hypothermic Postoperative Patients," *Anesth. Analg.*, 70:424–427, 1990.

Sessler, Daniel I.; "Mild Perioperative Hypothermia"; The New England Journal of Medicine; 336:1730–1737; Jun. 12, 1997.

Sharkey, A., et al.; "Inhibition of Postanesthetic Shivering with Radiant Heat"; *Anesthesiology*; 66(2);249–252, Feb. 1987.

Villarnaria, F. J., C. E. Baisden, A. Hillis, M. H. Rajab, and P. A. Rinaldi, "Forced–Air Warming is No More Effective than Conventional Methods for Raising Postoperative Core Temperature After Cardiac Surgery," *Journ. Cardiothoracic and Vascular Anesth.*, 11(6):708–711, Oct. 1997.

Zweifler, R. M. and D. L. Sessler, "Thermoregulatory Vasoconstriction and Shivering Impede Therapeutic Hypothermia in Acute Ischemic Stroke Patients," *Journ. Stroke and Cerebrovascular Diseases*, 6(2):100–104, 1996.

\* cited by examiner

ISOLATED SELECTIVE ORGAN COOLING APPARATUS

CROSS REFERENCE TO RELATED APPLICATIONS

This is a continuation patent application of co-pending U.S. patent application Ser. No. 09/292,532, filed on Apr. 15, 1999, and entitled Selective Organ Cooling Apparatus and Method"; which is a continuation-in-part patent application of U.S. patent application Ser. No. 09/103,342, filed on Jun. 23, 1998, and entitled "Selective Organ Cooling Catheter and Method of Using the Same", now U.S. Pat. No. 6,096,068; U.S. patent application Ser. No. 09/047,012, filed on Mar. 24, 1998, and entitled "Selective Organ Hypothermia Method and Apparatus", now U.S. Pat. No. 5,957,963; and U.S. patent application Ser. No. 09/052,545, filed on Mar. 31, 1998, and entitled "Circulating Fluid Hypothermia Method and Apparatus", now U.S. Pat. No. 6,231,595.

STATEMENT REGARDING FEDERALLY SPONSORED RESEARCH OR DEVELOPMENT

Not Applicable

BACKGROUND OF THE INVENTION

1. Field of the Invention

The present invention relates generally to the lowering and control of the temperature of a selected body organ. More particularly, the invention relates to a method and intravascular apparatus for cooling a selected organ, while isolating the cooling to the selected organ.

2. Background Information

Organs in the human body, such as the brain, kidney and heart, are maintained at a constant temperature of approximately 37° C. Hypothermia can be clinically defined as a core body temperature of 35° C. or less. Hypothermia is sometimes characterized further according to its severity. A body core temperature in the range of 33° C. to 35° C. is described as mild hypothermia. A body temperature of 28° C. to 32° C. is described as moderate hypothermia. A body core temperature in the range of 24° C. to 28° C. is described as severe hypothermia.

Hypothermia is uniquely effective in reducing brain injury caused by a variety of neurological insults and may eventually play an important role in emergency brain resuscitation. Experimental evidence has demonstrated that cerebral cooling improves outcome after global ischemia, focal ischemia, or traumatic brain injury. For this reason, hypothermia may be induced in order to reduce the effect of certain bodily injuries to the brain as well as other organs.

Cerebral hypothermia has traditionally been accomplished through whole body cooling to create a condition of total body hypothermia in the range of 20° C. to 30° C. However, the use of total body hypothermia risks certain deleterious systematic vascular effects. For example, total body hypothermia may cause severe derangement of the cardiovascular system, including low cardiac output, elevated systematic resistance, and ventricular fibrillation. Other side effects include renal failure, disseminated intravascular coagulation, and electrolyte disturbances. In addition to the undesirable side effects, total body hypothermia is difficult to administer.

Catheters have been developed which are inserted into the bloodstream of the patient in order to induce total body hypothermia. For example, U.S. Pat. No. 3,425,419 to Dato describes a method and apparatus of lowering and raising the temperature of the human body. Dato induces moderate hypothermia in a patient using a metallic catheter. The metallic catheter has an inner passageway through which a fluid, such as water, can be circulated. The catheter is inserted through the femoral vein and then through the inferior vena cava as far as the right atrium and the superior vena cava. The Dato catheter has an elongated cylindrical shape and is constructed from stainless steel. By way of example, Dato suggests the use of a catheter approximately 70 cm in length and approximately 6 mm in diameter. However, use of the Dato device implicates the negative effects of total body hypothermia described above.

Due to the problems associated with total body hypothermia, attempts have been made to provide more selective cooling. For example, cooling helmets or head gear have been used in an attempt to cool only the head rather than the patient's entire body. However, such methods rely on conductive heat transfer through the skull and into the brain. One drawback of using conductive heat transfer is that the process of reducing the temperature of the brain is prolonged. Also, it is difficult to precisely control the temperature of the brain when using conduction due to the temperature gradient that must be established externally in order to sufficiently lower the internal temperature. In addition, when using conduction to cool the brain, the face of the patient is also subjected to severe hypothermia, increasing discomfort and the likelihood of negative side effects. It is known that profound cooling of the face can cause similar cardiovascular side effects as total body cooling. From a practical standpoint, such devices are cumbersome and may make continued treatment of the patient difficult or impossible.

Selected organ hypothermia has been accomplished using extracorporeal perfusion, as detailed by Arthur E. Schwartz, M.D. et al., in *Isolated Cerebral Hypothermia by Single Carotid Artery Perfusion of Extracorporeally Cooled Blood in Baboons*, which appeared in Vol. 39, No. 3, Neurosurgery 577 (September, 1996). In this study, blood was continually withdrawn from baboons through the femoral artery. The blood was cooled by a water bath and then infused through a common carotid artery with its external branches occluded. Using this method, normal heart rhythm, systemic arterial blood pressure and arterial blood gas values were maintained during the hypothermia. This study showed that the brain could be selectively cooled to temperatures of 20° C. without reducing the temperature of the entire body. However, external circulation of blood is not a practical approach for treating humans because the risk of infection, need for anticoagulation, and risk of bleeding is too great. Further, this method requires cannulation of two vessels making it more cumbersome to perform particularly in emergency settings. Even more, percutaneous cannulation of the carotid artery is difficult and potentially fatal due to the associated arterial wall trauma. Finally, this method would be ineffective to cool other organs, such as the kidneys, because the feeding arteries cannot be directly cannulated percutaneously.

Selective organ hypothermia has also been attempted by perfusion of a cold solution such as saline or perfluorocarbons. This process is commonly used to protect the heart during heart surgery and is referred to as cardioplegia. Perfusion of a cold solution has a number of drawbacks, including a limited time of administration due to excessive volume accumulation, cost, and inconvenience of maintaining the perfusate and lack of effectiveness due to the temperature dilution from the blood. Temperature dilution by the blood is a particular problem in high blood flow organs such as the brain.

Therefore, a practical method and apparatus which lowers and controls the temperature of a selected organ satisfies a long-felt need. Further, it is desirable to have a temperature isolation method and apparatus for preventing the cooling of the selected organ from having an effect on the temperature of other parts of the body.

BRIEF SUMMARY OF THE INVENTION

The apparatus of the present invention can include a heat transfer element which can be used to apply cooling to the blood flowing in an artery feeding the selected organ. A similar heat transfer element may be used to supply warming to the blood flowing in a vein which returns blood from the selected organ, to prevent the cooling from affecting the temperature of other parts of the body. Alternatively, the warming operation can be accomplished by means of infusion of a warm saline solution into a vein, or by means of local heating of the vein with an external heat applicator, or by means of whole body warming with a heat blanket. Where used, the preferred heat transfer element, by way of example only, comprises first and second elongated, articulated segments, each segment having a turbulence-inducing exterior surface. A flexible joint can connect the first and second elongated segments. An inner coaxial lumen may be disposed within the first and second elongated segments and is capable of transporting a pressurized working fluid to a distal end of the first elongated segment. In addition, the first and second elongated segments may have a turbulence-inducing interior surface for inducing turbulence within the pressurized working fluid. The turbulence-inducing exterior surface may be adapted to induce turbulence within a free stream of blood flow when placed within an artery or vein. The turbulence-inducing exterior surface may be adapted to induce a turbulence intensity greater than 0.05 within a free stream blood flow. In one embodiment, the flexible joint comprises a bellows section which also allows for axial compression of the heat transfer element.

In one embodiment, the turbulence-inducing exterior surfaces of the heat transfer element comprise one or more helical ridges configured to have a depth which is greater than a thickness of a boundary layer of blood which develops within an arterial blood flow. Adjacent segments of the heat transfer element can be oppositely spiraled to increase turbulence. For instance, the first elongated heat transfer segment may comprise one or more helical ridges having a counter-clockwise twist, while the second elongated heat transfer segment comprises one or more helical ridges having a clockwise twist. Alternatively, of course, the first elongated heat transfer segment may comprise one or more clockwise helical ridges, and the second elongated heat transfer segment may comprise one or more counter-clockwise helical ridges. The first and second elongated, articulated segments may be formed from highly conductive materials.

In another embodiment, the turbulence-inducing exterior surface of the heat transfer element is adapted to induce turbulence throughout the duration of each pulse of a pulsatile blood flow when placed within an artery. In still another embodiment, the turbulence-inducing exterior surface of the heat transfer element is adapted to induce turbulence during at least 20% of the period of each cardiac cycle when placed within an artery.

The heat transfer device may also have a coaxial supply catheter with an inner catheter lumen coupled to the inner coaxial lumen within the first and second elongated heat transfer segments. A working fluid supply configured to dispense the pressurized working fluid may be coupled to the inner catheter lumen. The working fluid supply may be configured to produce the pressurized working fluid at a temperature of about 0° C. and at a pressure below about 5 atmospheres of pressure.

In yet another alternative embodiment, the heat transfer device may have three or more elongated, articulated, heat transfer segments having a turbulence-inducing exterior surface, with additional flexible joints connecting the additional elongated heat transfer segments. In one such embodiment, by way of example, the first and third elongated heat transfer segments may comprise clockwise helical ridges, and the second elongated heat transfer segment may comprise one or more counter-clockwise helical ridges. Alternatively, of course, the first and third elongated heat transfer segments may comprise counter-clockwise helical ridges, and the second elongated heat transfer segment may comprise one or more clockwise helical ridges.

The turbulence-inducing exterior surface of the heat transfer element may optionally include a surface coating or treatment to inhibit clot formation. One variation of the heat transfer element comprises a stent coupled to a distal end of the first elongated heat transfer segment.

The present invention also envisions a method of cooling the brain which comprises inserting a flexible, conductive cooling element into a carotid artery from a distal location, and providing a means of warming either the whole body or the blood returning from the brain in the jugular vein. Where warming is accomplished directly on the blood in the jugular vein, the method can include inserting a flexible, conductive warming element into the jugular vein. The method further includes circulating a working fluid through the flexible, conductive cooling element in order to selectively lower the temperature of the brain, and, where an intravenous warming element is used, circulating a warm working fluid through the flexible, conductive warming element. The flexible, conductive heat transfer element preferably absorbs more than about 25, 50 or 75 Watts of heat.

The method may also comprise the step of inducing turbulence within the free stream blood flow within the carotid artery, and, where applicable, the jugular vein. In one embodiment, the method includes the step of inducing blood turbulence with a turbulence intensity greater than about 0.05 within the vascular system. In another embodiment, the method includes the step of inducing blood turbulence throughout the duration of the period of the cardiac cycle within the vascular system. In yet another embodiment, the method comprises the step of inducing blood turbulence throughout the period of the cardiac cycle within the vascular system or during greater than about 20% of the period of the cardiac cycle. The step of circulating may comprise the step of inducing turbulent flow of the working fluid through the flexible, conductive heat transfer element. The pressure of the working fluid may be maintained below about 5 atmospheres of pressure.

The present invention also envisions a method for selectively cooling an organ in the body of a patient which comprises the steps of introducing a catheter, with a cooling element, into a blood vessel supplying the organ, the catheter having a diameter of about 4 mm or less, inducing free stream turbulence in blood flowing over the cooling element, and cooling the cooling element to remove heat from the blood to cool the organ while applying heat to prevent cooling other parts of the body. In one embodiment, the cooling step removes at least about 75 Watts of heat from the blood. In another embodiment, the cooling step removes at least about 100 Watts of heat from the blood. The organ being cooled may be the human brain.

The step of inducing free stream turbulence may induce a turbulence intensity greater than about 0.05 within the blood vessel. The step of inducing free stream turbulence may induce turbulence throughout the duration of each pulse of blood flow. The step of inducing free stream turbulence may induce turbulence for at least about 20% of the duration of each pulse of blood flow.

In one embodiment, the cooling or warming catheter has a flexible metal tip and the cooling or warming step occurs at the tip. The tip may have turbulence-inducing elongated heat transfer segments separated by bellows sections. The turbulence-inducing segments may comprise helical ridges which are configured to have a depth which is greater than a thickness of a boundary layer of blood which develops within the blood vessel. In another embodiment, the catheter has a tip at which the cooling or warming step occurs and the tip has turbulence-inducing elongated heat transfer segments that alternately spiral bias the surrounding blood flow in clockwise and counterclockwise directions.

The cooling or warming step may comprise the step of circulating a working fluid in through an inner lumen in the catheter and out through an outer, coaxial lumen. In one embodiment, the working fluid remains a liquid throughout the cycle. The working fluid may be aqueous.

The present invention also envisions a cooling or warming catheter comprising a catheter shaft having first and second lumens therein. The catheter also comprises a cooling or warming tip adapted to transfer heat to or from a working fluid circulated in through the first lumen and out through the second lumen, and turbulence-inducing structures on the tip capable of inducing free stream turbulence when the tip is inserted into a blood vessel. The turbulence-inducing structures may induce a turbulence intensity of at least about 0.05. The tip may be adapted to induce turbulence within the working fluid. The cooling catheter is capable of removing at least about 25 Watts of heat from an organ when inserted into a vessel supplying that organ, while cooling the tip with a working fluid that remains a liquid in the catheter. Alternatively, the catheter is capable of removing at least about 50 or 75 Watts of heat from an organ when inserted into a vessel supplying that organ, while cooling the tip with an aqueous working fluid. In one embodiment, in use, the tip has a diameter of about 4 mm or less. Optionally, the turbulence-inducing surfaces on the heat transfer segments comprise helical ridges which have a depth sufficient to disrupt the free stream blood flow in the blood vessel. Alternatively, the turbulence-inducing surfaces may comprise staggered protrusions from the outer surfaces of the heat transfer segments, which have a height sufficient to disrupt the free stream flow of blood within the blood vessel.

In another embodiment, a cooling or warming catheter may comprise a catheter shaft having first and second lumens therein, a cooling or warming tip adapted to transfer heat to or from a working fluid circulated in through the first lumen and out through the second lumen, and turbulence-inducing structures on the tip capable of inducing turbulence when the tip is inserted into a blood vessel. Alternatively, a cooling or warming catheter may comprise a catheter shaft having first and second lumens therein, a cooling or warming tip adapted to transfer heat to or from a working fluid circulated in through the first lumen and out through the second lumen, and structures on the tip capable of inducing free stream turbulence when the tip is inserted into a blood vessel. In another embodiment, a cooling or warming catheter may comprise a catheter shaft having first and second lumens therein, a cooling or warming tip adapted to transfer heat to or from a working fluid circulated in through the first lumen and out through the second lumen, and turbulence-inducing structures on the tip capable of inducing turbulence with an intensity greater than about 0.05 when the tip is inserted into a blood vessel.

The novel features of this invention, as well as the invention itself, will be best understood from the attached drawings, taken along with the following description, in which similar reference characters refer to similar parts, and in which:

DETAILED DESCRIPTION OF THE INVENTION

Figure 1:
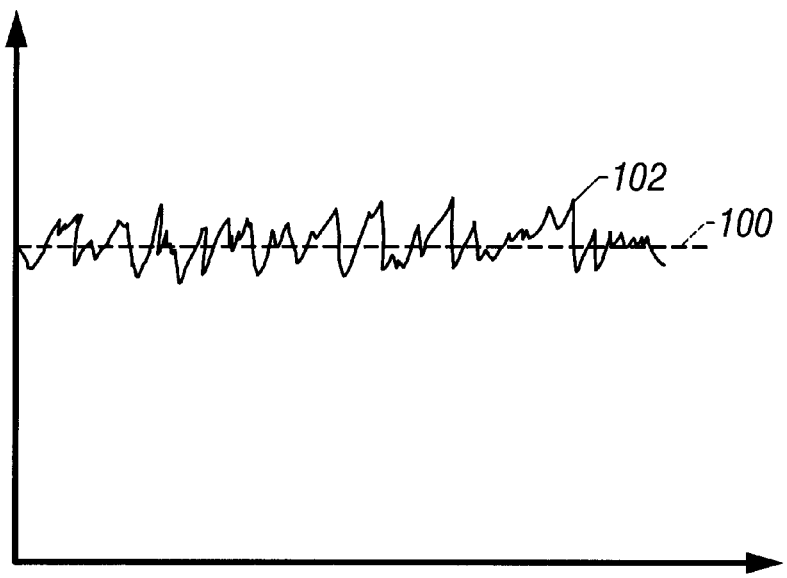
FIG. 1 is a graph illustrating the velocity of steady state turbulent flow as a function of time.

In order to intravascularly lower the temperature of a selected organ, a cooling element may be placed in the feeding artery of the organ to absorb heat from the blood flowing into the organ. This transfer of heat will cause a cooling of the selected organ. The cooling element must be small enough to fit within the feeding artery while still allowing a sufficient blood flow to reach the organ in order to avoid ischemic organ damage. A heat transfer element which selectively cools an organ should be capable of providing the necessary heat transfer rate to produce the desired cooling effect within the organ. By placing the heat transfer element within the feeding artery of an organ, the temperature of an organ can be controlled without significantly affecting the remaining parts of the body. The cooling of other parts of the body can be totally eliminated by judicious application of heat, such as in a vein returning from the selected organ. These points can be illustrated by using brain cooling as an example.

The common carotid artery supplies blood to the head and brain. The internal carotid artery branches off of the common carotid to directly supply blood to the brain. To selectively cool the brain, the cooling element is placed into the common carotid artery, or both the common carotid artery and the internal carotid artery. The internal diameter of the common carotid artery ranges from 6 to 8 mm and the length ranges from 80 to 120 mm. Thus, the cooling element residing in one of these arteries cannot be much larger than 4 mm in diameter in order to avoid occluding the vessel. The left and right internal jugular veins return blood from the brain. To prevent cooling of other parts of the body, the warming element is placed in either or both the left and right internal jugular veins. Alternatively, a warm saline solution can be infused into the jugular vein, or external heat can be applied, either at or near the jugular veins or to the whole body.

It is important that the intravascular heat transfer element, whether used for warming or cooling, be flexible in order to be placed within the feeding artery or the vein of an organ. Feeding arteries, like the carotid artery, branch off the aorta at various levels. Subsidiary arteries continue to branch off the initial branches. For example, the internal carotid artery is a small diameter artery that branches off of the common carotid artery near the angle of the jaw. Because the heat transfer element is typically inserted into a peripheral artery, such as the femoral artery, and accesses the feeding artery by initially passing though a series of one or more of these branches, the flexibility of the heat transfer element is an important characteristic of the heat transfer element. Further, the heat transfer element is ideally constructed from a highly thermally conductive material such as metal in order to facilitate heat transfer. The use of a highly thermally conductive material increases the heat transfer rate for a given temperature differential between the working fluid within the heat transfer element and the blood. This facilitates the use of a higher temperature coolant, or lower temperature warming fluid, within the heat transfer element, allowing safer working fluids, such as water, to be used. Highly thermally conductive materials, such as metals, tend to be rigid. Therefore, the design of the heat transfer element should facilitate flexibility in an inherently inflexible material.

In order to obtain the benefits of hypothermia described above, it is desirable to reduce the temperature of the blood flowing to the brain to between 30° C. and 32° C. Given that a typical brain has a blood flow rate through each carotid artery (right and left) of approximately 250–375 cubic centimeters per minute, the cooling element should absorb 75–175 Watts of heat when placed in one of the carotid arteries, in order to induce the desired cooling effect. It should be noted that smaller organs may have less blood flow in the supply artery and may require less heat transfer, such as 25 Watts.

When a heat transfer element is inserted coaxially into an artery or vein, the primary mechanism of heat transfer between the surface of the heat transfer element and the blood is forced convection. Convection relies upon the movement of fluid to transfer heat. Forced convection results when an external force causes motion within the fluid. In the case of arterial or venous flow, the beating heart causes the motion of the blood around the heat transfer element.

The magnitude of the heat transfer rate is proportional to the surface area of the heat transfer element, the temperature differential, and the heat transfer coefficient of the heat transfer element.

As noted above, the receiving artery or vein into which the heat transfer element is placed has a limited diameter and length. Thus, surface area of the heat transfer element must be limited, to avoid significant obstruction of the artery or vein, and to allow the heat transfer element to easily pass through the vascular system. For placement within the internal and common carotid artery, the cross sectional diameter of the heat transfer element is limited to about 4 mm, and its length is limited to approximately 10 cm.

The temperature differential can be increased by decreasing the surface temperature of the heat transfer element. However, the minimum allowable surface temperature is limited by the characteristics of blood. Blood freezes at approximately 0° C. When the blood approaches freezing, ice emboli may form in the blood which may lodge downstream, causing serious ischemic injury. Furthermore, reducing the temperature of the blood also increases its viscosity, which results in a small decrease in the value of the convection heat transfer coefficient. In addition, increased viscosity of the blood may result in an increase in the pressure drop within the artery, thus, compromising the flow of blood to the brain. Given the above constraints, it is advantageous to limit the minimum allowable surface temperature of the cooling element to approximately 5° C. This results in a maximum temperature differential between the blood stream and the cooling element of approximately 32° C. For other physiological reasons, there are limits on the maximum allowable surface temperature of the warming element.

The mechanisms by which the value of the convection heat transfer coefficient may be increased are complex. However, it is well known that the convection heat transfer coefficient increases with the level of turbulent kinetic energy in the fluid flow. Thus it is advantageous to have turbulent blood flow in contact with the heat transfer element.

FIG. 1 is a graph illustrating steady state turbulent flow. The vertical axis is the velocity of the flow. The horizontal axis represents time. The average velocity of the turbulent flow is shown by a line 100. The actual instantaneous velocity of the flow is shown by a curve 102.

Figure 3A:
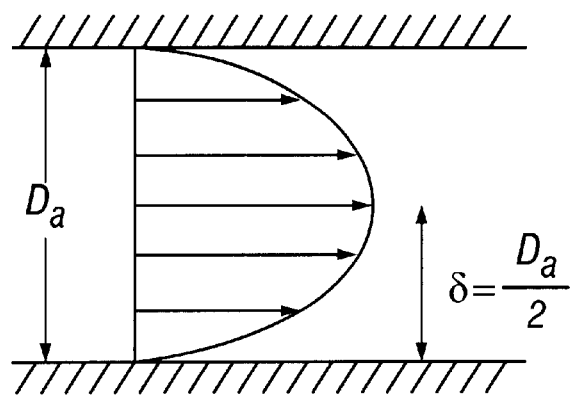
FIG. 3A is a velocity profile diagram showing a typical steady state Poiseuillean flow driven by a constant pressure gradient.

Under constant pressure conditions, steady flows in pipes are characterized as a balance between viscous stresses and the constant pressure gradient. Such flows are called Poiseuillean. FIG. 3A is a velocity profile diagram showing a typical steady state Poiseuillean flow driven by a constant pressure gradient. The velocity of the fluid across the pipe is shown in FIG. 3A by the parabolic curve and corresponding velocity vectors. The velocity of the fluid in contact with the wall of the pipe is zero. The boundary layer is the region of the flow in contact with the pipe surface in which viscous stresses are dominant. In steady state Poiseuillean flow, the boundary layer develops until it includes the whole pipe, i.e., the boundary layer thickness in FIG. 3A is one half of the diameter of the pipe.

Under conditions of Poiseuillean flow, the Reynolds number, the ratio of inertial forces to viscous forces, can be used to characterize the level of turbulent kinetic energy existing in the flow. For Poiseuillean flows, Reynolds numbers must be greater than about 2300 to cause a transition from laminar to turbulent flow. Further, when the Reynolds number is greater than about 2000, the boundary layer is receptive to "tripping". Tripping is a process by which a small perturbation in the boundary layer can create turbulent conditions. The receptivity of a boundary layer to "tripping" is proportional to the Reynolds number and is nearly zero for Reynolds numbers less than 2000.

Figure 2A:
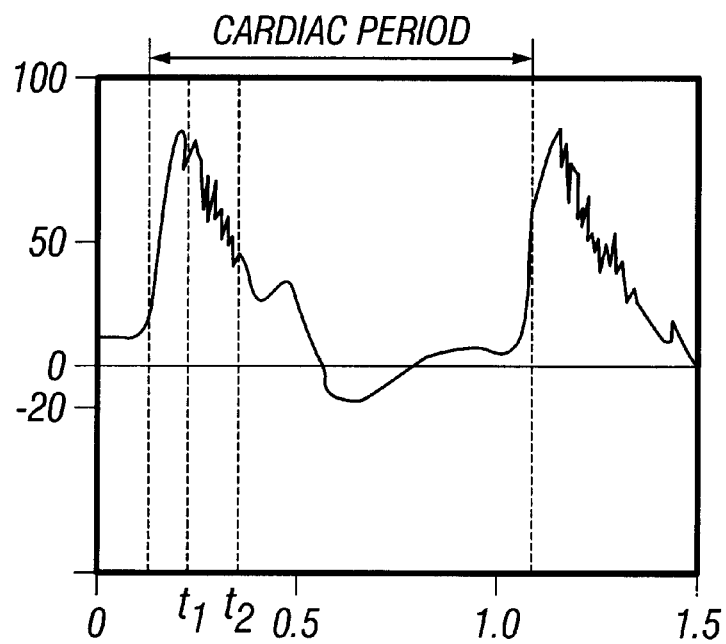
FIG. 2A is a graph showing the velocity of the blood flow within an artery as a function of time.

In contrast with the steady Poiseuillean flow, the blood flow in arteries is induced by the beating heart and is therefore pulsatile. FIG. 2A is a graph showing the velocity of the blood flow within an artery as a function of time. The beating heart provides pulsatile flow with an approximate period of 0.5 to 1 second. This is known as the period of the cardiac cycle. The horizontal axis in FIG. 2A represents time in seconds and the vertical axis represents the average velocity of blood in centimeters per second. Although very high velocities are reached at the peak of the pulse, the high velocity occurs for only a small portion of the cycle. In fact, the velocity of the blood reaches zero in the carotid artery at the end of a pulse and temporarily reverses.

Figure 3B:
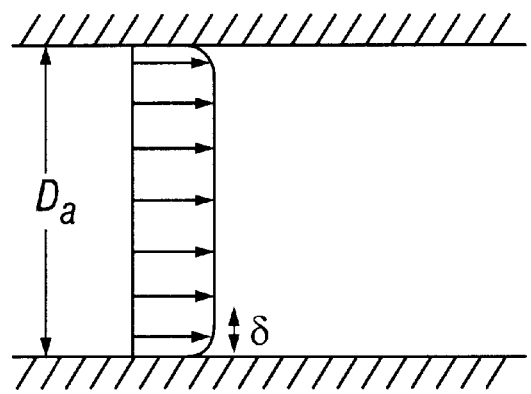
FIG. 3B is a velocity profile diagram showing blood flow velocity within an artery, averaged over the duration of the cardiac pulse.

Because of the relatively short duration of the cardiac pulse, the blood flow in the arteries does not develop into the classic Poiseuillean flow. FIG. 3B is a velocity profile diagram showing blood flow velocity within an artery averaged over the cardiac pulse. The majority of the flow within the artery has the same velocity. The boundary layer where the flow velocity decays from the free stream value to zero is very thin, typically ⅙ to ¹⁄₂₀ of the diameter of the artery, as opposed to one half of the diameter of the artery in the Poiseuillean flow condition.

As noted above, if the flow in the artery were steady rather than pulsatile, the transition from laminar to turbulent flow would occur when the value of the Reynolds number exceeds about 2,000. However, in the pulsatile arterial flow, the value of the Reynolds number varies during the cardiac cycle, just as the flow velocity varies. In pulsatile flows, due to the enhanced stability associated with the acceleration of the free stream flow, the critical value of the Reynolds number at which the unstable modes of motion grow into turbulence is found to be much higher, perhaps as high as 9,000.

The blood flow in the arteries of interest remains laminar over more than 80% of the cardiac cycle. Referring again to FIG. 2A, the blood flow is turbulent from approximately time $t_1$ until time $t_2$ during a small portion of the descending systolic flow, which is less than 20% of the period of the cardiac cycle. If a heat transfer element is placed inside the artery, heat transfer will be facilitated during this short interval. However, to transfer the necessary heat to cool the brain, turbulent kinetic energy should be produced in the blood stream and sustained throughout the entire period of the cardiac cycle.

Figure 3C:
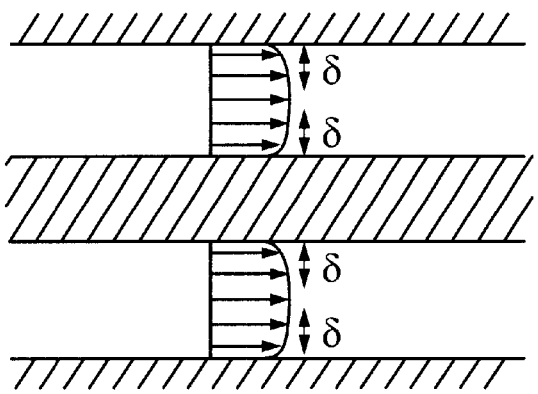
FIG. 3C is a velocity profile diagram showing blood flow velocity within an artery, averaged over the duration of the cardiac pulse, after insertion of a smooth heat transfer element within the artery.

A thin boundary layer has been shown to form during the cardiac cycle. This boundary layer will form over the surface of a smooth heat transfer element. FIG. 3C is a velocity profile diagram showing blood flow velocity within an artery, averaged over the cardiac pulse, after insertion of a smooth heat transfer element within the artery. In FIG. 3C, the diameter of the heat transfer element is about one half of the diameter of the artery. Boundary layers develop adjacent to the heat transfer element as well as next to the walls of the artery. Each of these boundary layers has approximately the same thickness as the boundary layer which would have developed at the wall of the artery in the absence of the heat transfer element. The free stream flow region is developed in an annular ring around the heat transfer element.

One way to increase the heat transfer rate is to create a turbulent boundary layer on the heat transfer element surface. However, turbulence in the very thin boundary layer will not produce sufficient kinetic energy to produce the necessary heat transfer rate. Therefore, to induce sufficient turbulent kinetic energy to increase the heat transfer rate sufficiently to cool the brain, and to subsequently warm the blood flow in the vein, a stirring mechanism, which abruptly changes the direction of velocity vectors, should be utilized. This can create high levels of turbulence intensity in the free stream, thereby sufficiently increasing the heat transfer rate.

Figure 2B:
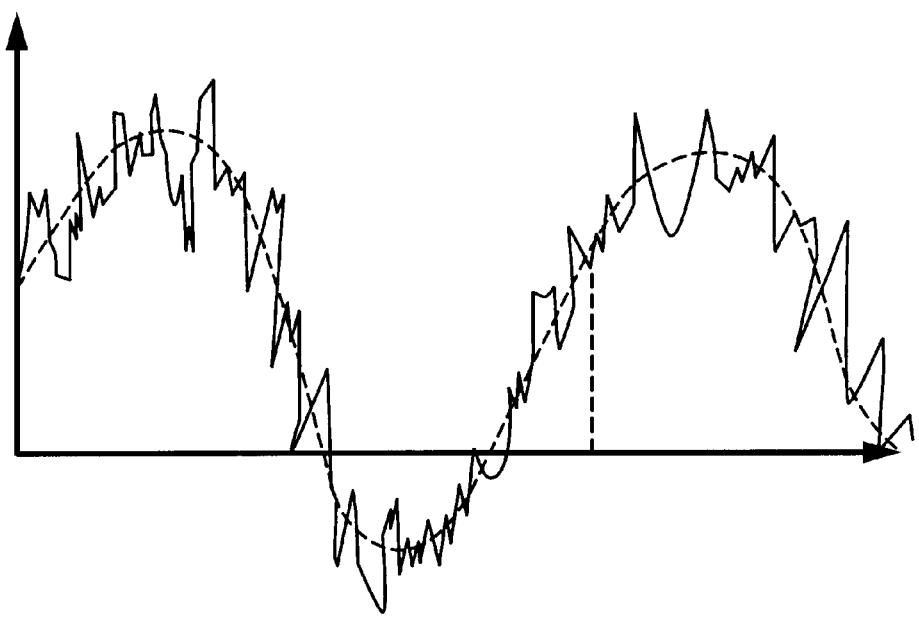
FIG. 2B is a graph illustrating the velocity of steady state turbulent flow under pulsatile conditions as a function of time, similar to arterial blood flow.

This turbulence intensity should ideally be sustained for a significant portion of the cardiac cycle. Further, turbulent kinetic energy should ideally be created throughout the free stream and not just in the boundary layer. FIG. 2B is a graph illustrating the velocity of continually turbulent flow under pulsatile conditions as a function of time, which would result in optimal heat transfer in arterial blood flow. Turbulent velocity fluctuations are seen throughout the cycle as opposed to the short interval of fluctuations seen in FIG. 2A between time $t_1$ and time $t_2$. These velocity fluctuations are found within the free stream. The turbulence intensity shown in FIG. 2B is at least 0.05. In other words, the instantaneous velocity fluctuations deviate from the mean velocity by at least 5%. Although, ideally, turbulence is created throughout the entire period of the cardiac cycle, the benefits of turbulence are also obtained if the turbulence is sustained for only 75%, 50% or even as low as 30% or 20% of the cardiac cycle.

Figure 2C:
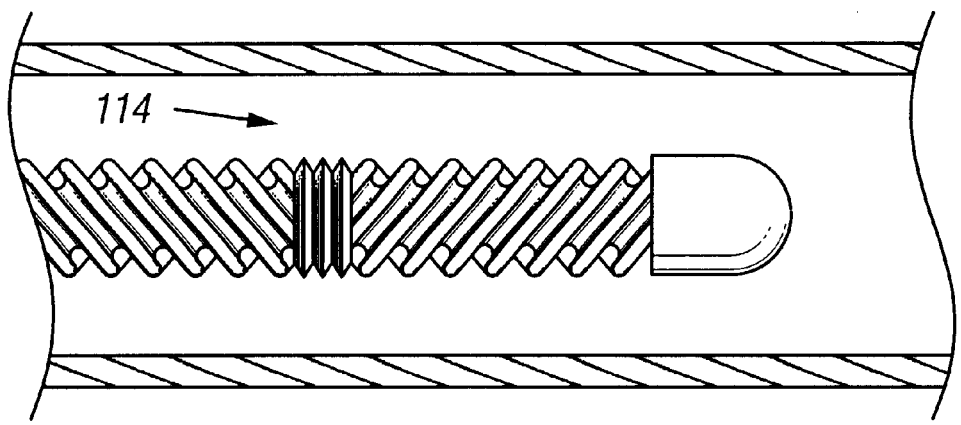
FIG. 2C is an elevation view of a turbulence inducing heat transfer element within an artery.

To create the desired level of turbulence intensity in the blood free stream during the whole cardiac cycle, one embodiment of the invention uses a modular design. This design creates helical blood flow and produces a high level of turbulence in the free stream by periodically forcing abrupt changes in the direction of the helical blood flow. FIG. 2C is a perspective view of such a turbulence inducing heat transfer element within an artery. Turbulent flow would be found at point 114, in the free stream area. The abrupt changes in flow direction are achieved through the use of a series of two or more heat transfer segments, each comprised of one or more helical ridges. To affect the free stream, the depth of the helical ridge is larger than the thickness of the boundary layer which would develop if the heat transfer element had a smooth cylindrical surface.

The use of periodic abrupt changes in the helical direction of the blood flow in order to induce strong free stream turbulence may be illustrated with reference to a common clothes washing machine. The rotor of a washing machine spins initially in one direction causing laminar flow. When the rotor abruptly reverses direction, significant turbulent kinetic energy is created within the entire wash basin as the changing currents cause random turbulent motion within the clothes-water slurry.

Figure 4:
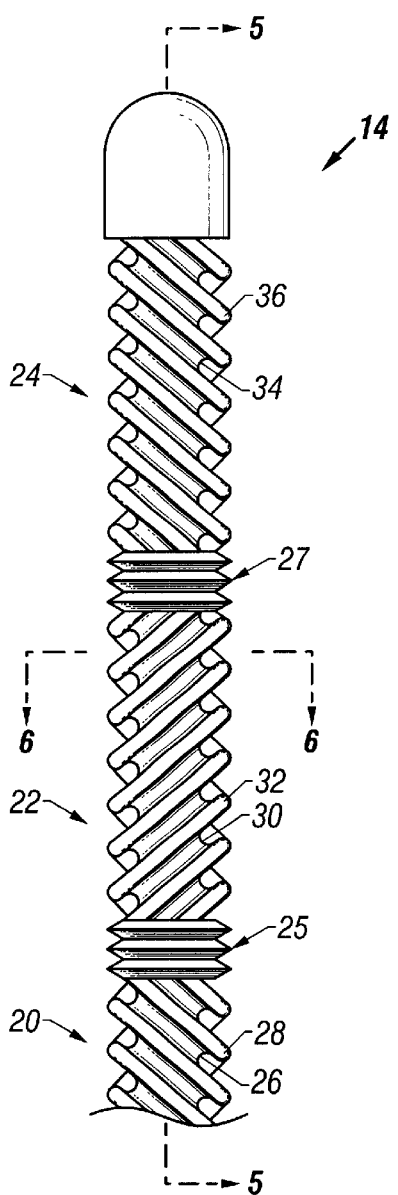
FIG. 4 is an elevation view of one embodiment of a heat transfer element according to the invention.

FIG. 4 is an elevation view of one embodiment of a cooling element 14 according to the present invention. A similar design can be used in the warming element 114 shown in FIG. 10. The heat transfer element 14 is comprised of a series of elongated, articulated segments or modules 20, 22, 24. Three such segments are shown in this embodiment, but two or more such segments could be used without departing from the spirit of the invention. As seen in FIG. 4, a first elongated heat transfer segment 20 is located at the proximal end of the heat transfer element 14. A turbulence-inducing exterior surface of the segment 20 comprises four parallel helical ridges 28 with four parallel helical grooves 26 therebetween. One, two, three, or more parallel helical ridges 28 could also be used without departing from the spirit of the present invention. In this embodiment, the helical ridges 28 and the helical grooves 26 of the heat transfer segment 20 have a left hand twist, referred to herein as a counter-clockwise spiral or helical rotation, as they proceed toward the distal end of the heat transfer segment 20.

The first heat transfer segment 20 is coupled to a second elongated heat transfer segment 22 by a first bellows section 25, which provides flexibility and compressibility. The second heat transfer segment 22 comprises one or more helical ridges 32 with one or more helical grooves 30 therebetween. The ridges 32 and grooves 30 have a right hand, or clockwise, twist as they proceed toward the distal end of the heat transfer segment 22. The second heat transfer segment 22 is coupled to a third elongated heat transfer segment 24 by a second bellows section 27. The third heat transfer segment 24 comprises one or more helical ridges 36 with one or more helical grooves 34 therebetween. The helical ridge 36 and the helical groove 34 have a left hand, or counter-clockwise, twist as they proceed toward the distal end of the heat transfer segment 24. Thus, successive heat transfer segments 20, 22, 24 of the heat transfer element 14 alternate between having clockwise and counterclockwise helical twists. The actual left or right hand twist of any particular segment is immaterial, as long as adjacent segments have opposite helical twist.

In addition, the rounded contours of the ridges 28, 32, 36 also allow the heat transfer element 14 to maintain a relatively atraumatic profile, thereby minimizing the possibility of damage to the blood vessel wall. A heat transfer element according to the present invention may be comprised of two, three, or more heat transfer segments.

The bellows sections 25, 27 are formed from seamless and nonporous materials, such as metal, and therefore are impermeable to gas, which can be particularly important, depending on the type of working fluid which is cycled through the heat transfer element 14. The structure of the bellows sections 25, 27 allows them to bend, extend and compress, which increases the flexibility of the heat transfer element 14 so that it is more readily able to navigate through blood vessels. The bellows sections 25, 27 also provide for axial compression of the heat transfer element 14, which can limit the trauma when the distal end of the heat transfer element 14 abuts a blood vessel wall. The bellows sections 25, 27 are also able to tolerate cryogenic temperatures without a loss of performance.

The exterior surfaces of the heat transfer element 14 can be made from metal, and may comprise very high thermal conductivity materials such as nickel, thereby facilitating heat transfer. Alternatively, other metals such as stainless steel, titanium, aluminum, silver, copper and the like, can be used, with or without an appropriate coating or treatment to enhance biocompatibility or inhibit clot formation. Suitable biocompatible coatings include, e.g., gold, platinum or polymer paralyene. The heat transfer element 14 may be manufactured by plating a thin layer of metal on a mandrel that has the appropriate pattern. In this way, the heat transfer element 14 may be manufactured inexpensively in large quantities, which is an important feature in a disposable medical device.

Because the heat transfer element 14 may dwell within the blood vessel for extended periods of time, such as 24–48 hours or even longer, it may be desirable to treat the surfaces of the heat transfer element 14 to avoid clot formation. In particular, one may wish to treat the bellows sections 25, 27 because stagnation of the blood flow may occur in the convolutions, thus allowing clots to form and cling to the surface to form a thrombus. One means by which to prevent thrombus formation is to bind an antithrombogenic agent to the surface of the heat transfer element 14. For example, heparin is known to inhibit clot formation and is also known to be useful as a biocoating. Alternatively, the surfaces of the heat transfer element 14 may be bombarded with ions such as nitrogen. Bombardment with nitrogen can harden and smooth the surface and, thus prevent adherence of clotting factors to the surface.

Figure 5:
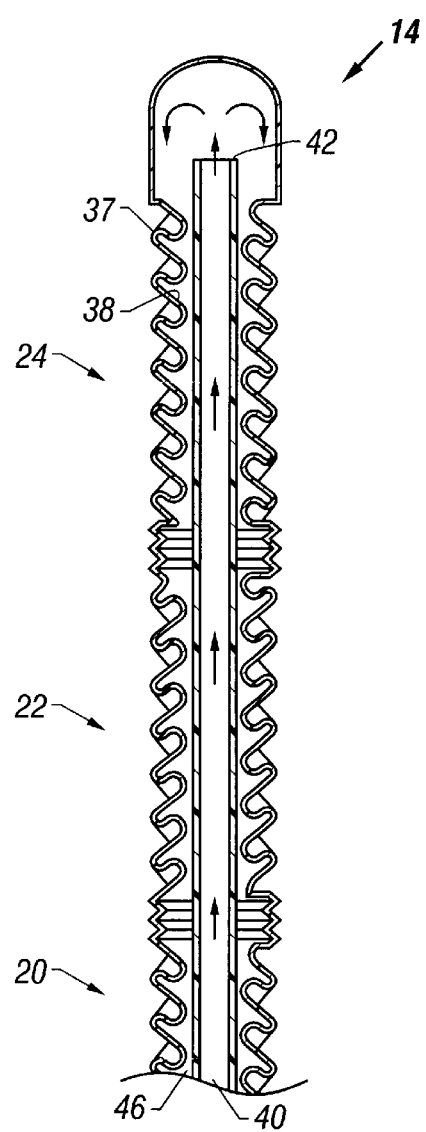
FIG. 5 is longitudinal section view of the heat transfer element of FIG. 4.

FIG. 5 is a longitudinal sectional view of the heat transfer element 14 of an embodiment of the invention, taken along line 5—5 in FIG. 4. Some interior contours are omitted for purposes of clarity. An inner tube 42 creates an inner coaxial lumen 42 and an outer coaxial lumen 46 within the heat transfer element 14. Once the heat transfer element 14 is in place in the blood vessel, a working fluid such as saline or other aqueous solution may be circulated through the heat transfer element 14. Fluid flows up a supply catheter into the inner coaxial lumen 40. At the distal end of the heat transfer element 14, the working fluid exits the inner coaxial lumen 40 and enters the outer lumen 46. As the working fluid flows through the outer lumen 46, heat is transferred from the working fluid to the exterior surface 37 of the heat transfer element 14. Because the heat transfer element 14 is constructed from a high conductivity material, the temperature of its exterior surface 37 may reach very close to the temperature of the working fluid. The tube 42 may be formed as an insulating divider to thermally separate the inner lumen 40 from the outer lumen 46. For example, insulation may be achieved by creating longitudinal air channels in the wall of the insulating tube 42. Alternatively, the insulating tube 42 may be constructed of a non-thermally conductive material like polytetrafluoroethylene or some other polymer.

It is important to note that the same mechanisms that govern the heat transfer rate between the exterior surface 37 of the heat transfer element 14 and the blood also govern the heat transfer rate between the working fluid and the interior surface 38 of the heat transfer element 14. The heat transfer characteristics of the interior surface 38 are particularly important when using water, saline or other fluid which remains a liquid as the working fluid. Other coolants such as freon undergo nucleate boiling and create turbulence through a different mechanism. Saline is a safe working fluid, because it is non-toxic, and leakage of saline does not result in a gas embolism, which could occur with the use of boiling refrigerants. Since turbulence in the working fluid is enhanced by the shape of the interior surface 38 of the heat transfer element 14, the working fluid can be delivered to the cooling element 14 at a warmer temperature and still achieve the necessary cooling rate. Similarly, since turbulence in the working fluid is enhanced by the shape of the interior surface of the heat transfer element, the working fluid can be delivered to the warming element 14 at a cooler temperature and still achieve the necessary warming rate.

This has a number of beneficial implications in the need for insulation along the catheter shaft length. Due to the decreased need for insulation, the catheter shaft diameter can be made smaller. The enhanced heat transfer characteristics of the interior surface of the heat transfer element 14 also allow the working fluid to be delivered to the heat transfer element 14 at lower flow rates and lower pressures. High pressures may make the heat transfer element stiff and cause it to push against the wall of the blood vessel, thereby shielding part of the exterior surface 37 of the heat transfer element 14 from the blood. Because of the increased heat transfer characteristics achieved by the alternating helical ridges 28, 32, 36, the pressure of the working fluid may be as low as 5 atmospheres, 3 atmospheres, 2 atmospheres or even less than 1 atmosphere.

Figure 6:
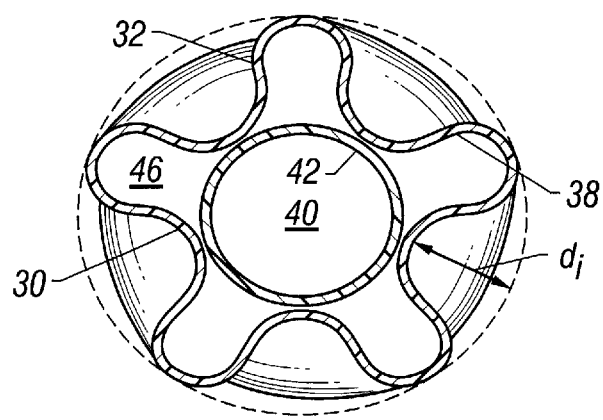
FIG. 6 is a transverse section view of the heat transfer element of FIG. 4.

FIG. 6 is a transverse sectional view of the heat transfer element 14 of the invention, taken at a location denoted by the line 6—6 in FIG. 4. FIG. 6 illustrates a five lobed embodiment, whereas FIG. 4 illustrates a four-lobed embodiment. As mentioned earlier, any number of lobes might be used. In FIG. 6, the coaxial construction of the heat transfer element 14 is clearly shown. The inner coaxial lumen 40 is defined by the insulating coaxial tube 42. The outer lumen 46 is defined by the exterior surface of the insulating coaxial tube 42 and the interior surface 38 of the heat transfer element 14. In addition, the helical ridges 32 and helical grooves 30 may be seen in FIG. 6. As noted above, in the preferred embodiment, the depth of the grooves, $d_\lambda$, is greater than the boundary layer thickness which would have developed if a cylindrical heat transfer element were introduced. For example, in a heat transfer element 14 with a 4 mm outer diameter, the depth of the invaginations, $d_\lambda$, may be approximately equal to 1 mm if designed for use in the carotid artery. Although FIG. 6 shows four ridges and four grooves, the number of ridges and grooves may vary. Thus, heat transfer elements with 1, 2, 3, 4, 5, 6, 7, 8 or more ridges are specifically contemplated.

Figure 7:
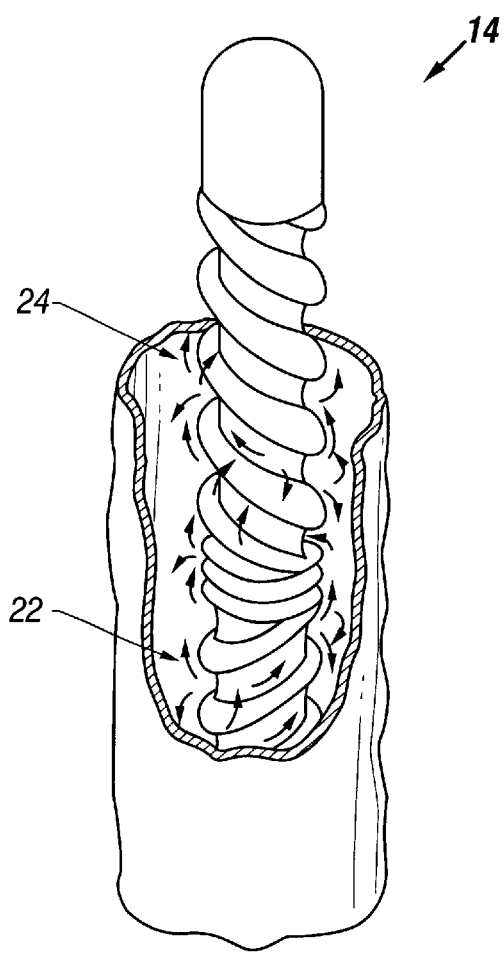
FIG. 7 is a perspective view of the heat transfer element of FIG. 4 in use within a blood vessel.

FIG. 7 is a perspective view of a heat transfer element 14 in use within a blood vessel, showing only one helical lobe per segment for purposes of clarity. Beginning from the proximal end of the heat transfer element (not shown in FIG. 7), as the blood moves forward during the systolic pulse, the first helical heat transfer segment 20 induces a counter-clockwise rotational inertia to the blood. As the blood reaches the second segment 22, the rotational direction of the inertia is reversed, causing turbulence within the blood. Further, as the blood reaches the third segment 24, the rotational direction of the inertia is again reversed. The sudden changes in flow direction actively reorient and randomize the velocity vectors, thus ensuring turbulence throughout the bloodstream. During turbulent flow, the velocity vectors of the blood become more random and, in some cases, become perpendicular to the axis of the artery. In addition, as the velocity of the blood within the artery decreases and reverses direction during the cardiac cycle, additional turbulence is induced and turbulent motion is sustained throughout the duration of each pulse through the same mechanisms described above.

Thus, a large portion of the volume of warn blood in the vessel is actively brought in contact with the heat transfer element 14, where it can be cooled by direct contact rather than being cooled largely by conduction through adjacent laminar layers of blood. As noted above, the depth of the grooves 26, 30, 34 (FIG. 4) is greater than the depth of the boundary layer which would develop if a straight-walled heat transfer element were introduced into the blood stream. In this way, free stream turbulence is induced. In the preferred embodiment, in order to create the desired level of turbulence in the entire blood stream during the whole cardiac cycle, the heat transfer element 14 creates a turbulence intensity greater than about 0.05. The turbulence intensity may be greater than 0.05, 0.06, 0.07 or up to 0.10 or 0.20 or greater.

Referring back to FIG. 4, the heat transfer element 14 has been designed to address all of the design criteria discussed above. First, the heat transfer element 14 is flexible and is made of a highly conductive material. The flexibility is provided by a segmental distribution of bellows sections 25, 27 which provide an articulating mechanism. Bellows have a known convoluted design which provides flexibility. Second, the exterior surface area 37 has been increased through the use of helical ridges 28, 32, 36 and helical grooves 26, 30, 34. The ridges also allow the heat transfer element 14 to maintain a relatively atraumatic profile, thereby minimizing the possibility of damage to the vessel wall. Third, the heat transfer element 14 has been designed to promote turbulent kinetic energy both internally and externally. The modular or segmental design allows the direction of the invaginations to be reversed between segments. The alternating helical rotations create an alternating flow that results in mixing the blood in a manner analogous to the mixing action created by the rotor of a washing machine that switches directions back and forth. This mixing action is intended to promote high level turbulent kinetic energy to enhance the heat transfer rate. The alternating helical design also causes beneficial mixing, or turbulent kinetic energy, of the working fluid flowing internally.

Figure 8:
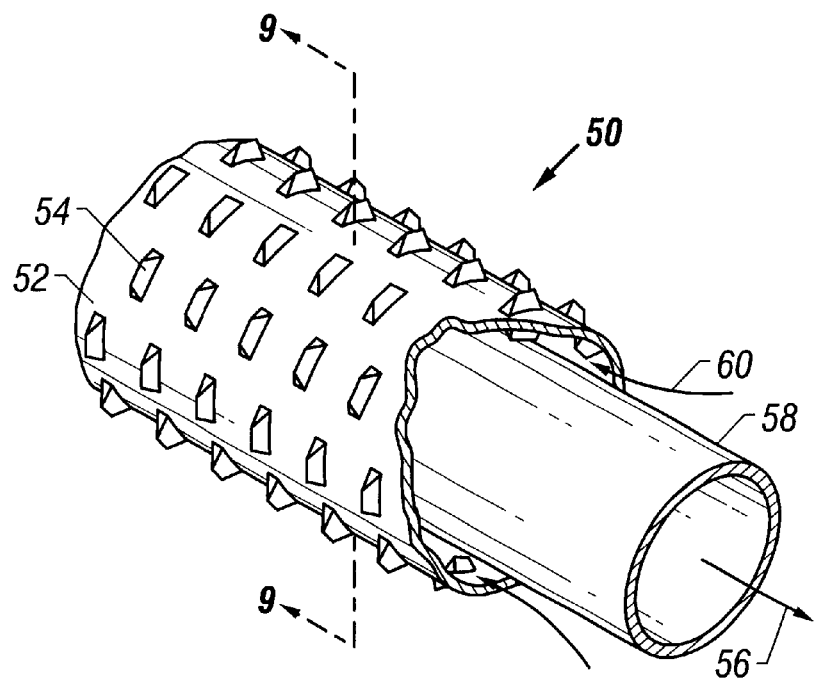
FIG. 8 is a cut-away perspective view of an alternative embodiment of a heat transfer element according to the invention.

FIG. 8 is a cut-away perspective view of an alternative embodiment of a heat transfer element 50. An external surface 52 of the heat transfer element 50 is covered with a series of axially staggered protrusions 54. The staggered nature of the outer protrusions 54 is readily seen with reference to FIG. 9 which is a transverse cross-sectional view taken at a location denoted by the line 9—9 in FIG. 8. In order to induce free stream turbulence, the height, $d_p$, of the staggered outer protrusions 54 is greater than the thickness of the boundary layer which would develop if a smooth heat transfer element had been introduced into the blood stream. As the blood flows along the external surface 52, it collides with one of the staggered protrusions 54 and a turbulent wake flow is created behind the protrusion. As the blood divides and swirls along side of the first staggered protrusion 54, its turbulent wake encounters another staggered protrusion 54 within its path preventing the re-lamination of the flow and creating yet more turbulence. In this way, the velocity vectors are randomized and turbulence is created not only in the boundary layer but throughout the free stream. As is the case with the preferred embodiment, this geometry also induces a turbulent effect on the internal working fluid flow.

Figure 9:
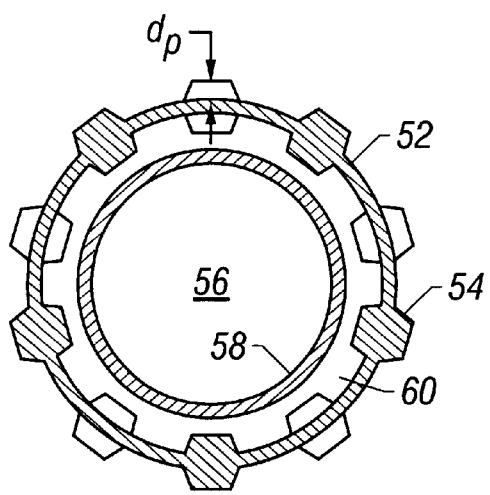
FIG. 9 is a transverse section view of the heat transfer element of FIG. 8.

A working fluid is circulated up through an inner coaxial lumen 56 defined by an insulating coaxial tube 58 to a distal tip of the heat transfer element 50. The working fluid then traverses an outer coaxial lumen 60 in order to transfer heat to the exterior surface 52 of the heat transfer element 50. The inside surface of the heat transfer element 50 is similar to the exterior surface 52, in order to induce turbulent flow of the working fluid. The inner protrusions can be aligned with the outer protrusions 54, as shown in FIG. 9, or they can be offset from the outer protrusions 54, as shown in FIG. 8.

Figure 10:
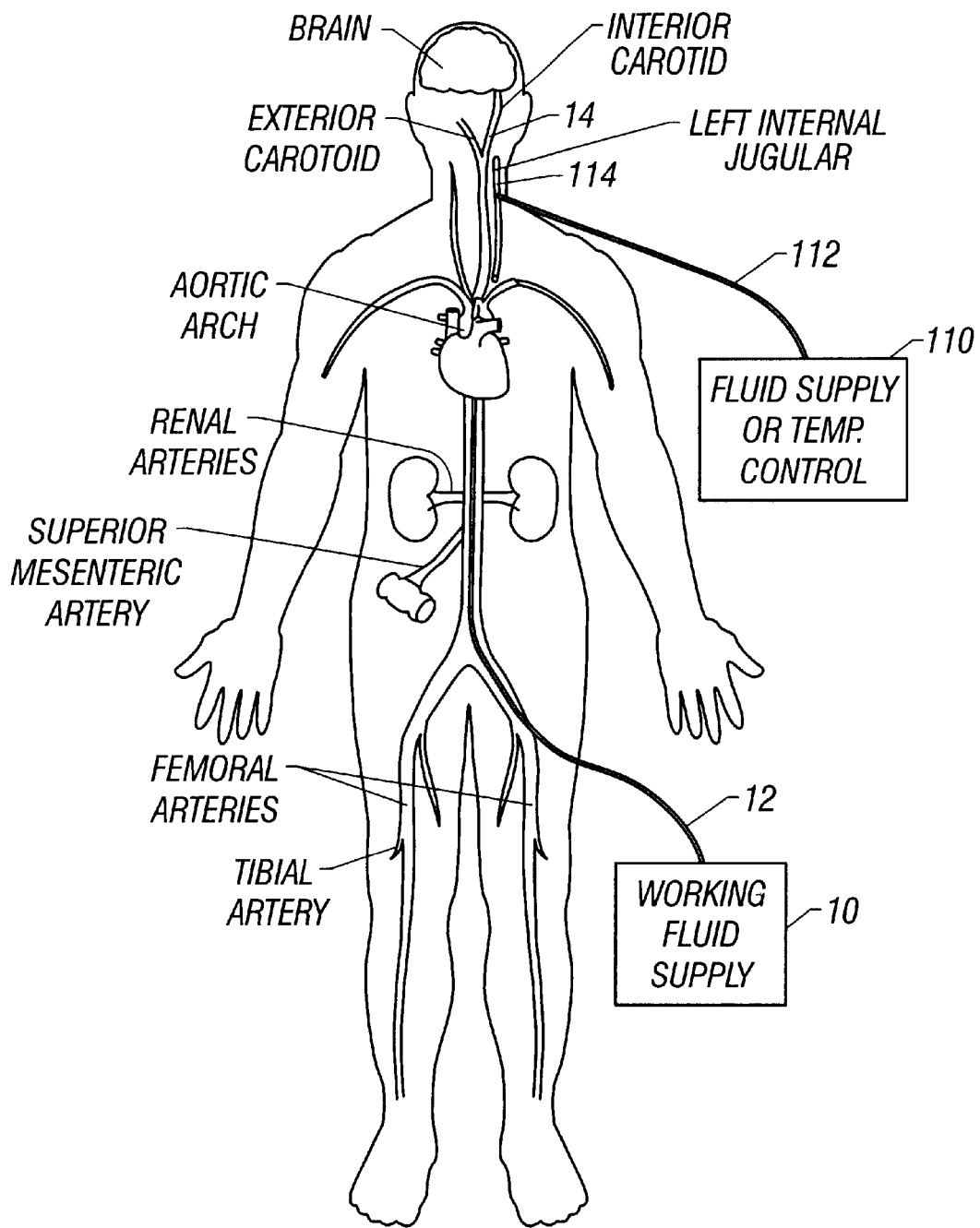
FIG. 10 is a schematic representation of the heat transfer element being used in one embodiment to cool the brain of a patient and to warm the blood returning from the brain in the jugular vein.

FIG. 10 is a schematic representation of the invention being used to cool the brain of a patient, and to warm the blood returning from the brain in the jugular vein. The selective organ hypothermia apparatus shown in FIG. 10 includes a first working fluid supply 10, preferably supplying a chilled liquid such as water, alcohol or a halogenated hydrocarbon, a first supply catheter 12 and the cooling element 14. The first supply catheter 12 has a coaxial construction. An inner coaxial lumen within the first supply catheter 12 receives coolant from the first working fluid supply 10. The coolant travels the length of the first supply catheter 12 to the cooling element 14 which serves as the cooling tip of the catheter. At the distal end of the cooling element 14, the coolant exits the insulated interior lumen and traverses the length of the cooling element 14 in order to decrease the temperature of the cooling element 14. The coolant then traverses an outer lumen of the first supply catheter 12 so that it may be disposed of or recirculated. The first supply catheter 12 is a flexible catheter having a diameter sufficiently small to allow its distal end to be inserted percutaneously into an accessible artery such as the femoral artery of a patient as shown in FIG. 10. The first supply catheter 12 is sufficiently long to allow the cooling element 14 at the distal end of the first supply catheter 12 to be passed through the vascular system of the patient and placed in the internal carotid artery or other small artery. The method of inserting the catheter into the patient and routing the cooling element 14 into a selected artery is well known in the art.

Although the working fluid supply 10 is shown as an exemplary cooling device, other devices and working fluids may be used. For example, in order to provide cooling, freon, perfluorocarbon, water, or saline may be used, as well as other such coolants.

The cooling element can absorb or provide over 75 Watts of heat to the blood stream and may absorb or provide as much as 100 Watts, 150 Watts, 170 Watts or more. For example, a cooling element with a diameter of 4 mm and a length of approximately 10 cm using ordinary saline solution chilled so that the surface temperature of the heat transfer element is approximately 5° C. and pressurized at 2 atmospheres can absorb about 100 Watts of energy from the bloodstream. Smaller geometry heat transfer elements may be developed for use with smaller organs which provide 60 Watts, 50 Watts, 25 Watts or less of heat transfer.

FIG. 10 also shows a second working fluid supply 110, preferably supplying a warm liquid such as water, a second supply catheter 112 and the warming element 114, which can be similar or identical to the cooling element 14. The second supply catheter 112 has a coaxial construction. An inner coaxial lumen within the second supply catheter 112 receives warm fluid from the second working fluid supply 110. The fluid travels the length of the second supply catheter 112 to the warming element 114 which serves as the warming tip of the catheter. At the distal end of the warming element 114, the fluid exits the insulated interior lumen and traverses the length of the warming element 114 in order to increase the temperature of the warming element 114. The fluid then traverses an outer lumen of the second supply catheter 112 so that it may be disposed of or recirculated. The second supply catheter 112 is a flexible catheter having a diameter sufficiently small to allow its distal end to be inserted percutaneously into an accessible vein such as the left internal jugular vein of a patient as shown in FIG. 10.

As an alternative, the warming element 114 can be an electrical resistance heater controlled by a controller represented by item 110.

The practice of the present invention is illustrated in the following non-limiting example.

Exemplary Procedure

1. The patient is initially assessed, resuscitated, and stabilized.
2. The procedure is carried out in an angiography suite or surgical suite equipped with fluoroscopy.
3. Because the cooling catheter is placed into the common carotid artery, it is important to determine the presence of stenotic atheromatous lesions. A carotid duplex (doppler/ultrasound) scan can quickly and non-invasively make this determinations. The ideal location for placement of the catheter is in the left carotid so this may be scanned first. If disease is present, then the right carotid artery can be assessed. This test can be used to detect the presence of proximal common carotid lesions by observing the slope of the systolic upstroke and the shape of the pulsation. Although these lesions are rare, they could inhibit the placement of the catheter. Examination of the peak blood flow velocities in the internal carotid can determine the presence of internal carotid artery lesions. Although the catheter is placed proximally to such lesions, the catheter may exacerbate the compromised blood flow created by these lesions. Peak systolic velocities greater that 130 cm/sec and peak diastolic velocities >100 cm/sec in the internal indicate the presence of at least 70% stenosis. Stenosis of 70% or more may warrant the placement of a stent to open up the internal artery diameter.
4. The ultrasound can also be used to determine the vessel diameter and the blood flow and the catheter with the appropriately sized heat transfer element could be selected.
5. After assessment of the arteries, the patients inguinal region is sterilely prepped and infiltrated with lidocaine.
6. The femoral artery is cannulated and a guide wire may be inserted to the desired carotid artery. Placement of the guide wire is confirmed with fluoroscopy.
7. An angiographic catheter can be fed over the wire and contrast media injected into the artery to further to assess the anatomy of the carotid.
8. Alternatively, the femoral artery is cannulated and a 10–12.5 french (f) introducer sheath is placed.
9. A guide catheter is placed into the desired common carotid artery. If a guiding catheter is placed, it can be used to deliver contrast media directly to further assess carotid anatomy.
10. A 10 f–12 f (3.3–4.0 mm) (approximate) cooling catheter is subsequently filled with saline and all air bubbles are removed.
11. The cooling catheter is placed into the carotid artery via the guiding catheter or over the guidewire. Placement is confirmed with fluoroscopy.
12. Alternatively, the cooling catheter tip is shaped (angled or curved approximately 45 degrees), and the cooling catheter shaft has sufficient pushability and torqueability to be placed in the carotid without the aid of a guide wire or guide catheter.
13. The cooling catheter is connected to a pump circuit also filled with saline and free from air bubbles. The pump circuit has a heat exchange section that is immersed into a water bath and tubing that is connected to a peristaltic pump. The water bath is chilled to approximately 0° C.
14. Cooling is initiated by starting the pump mechanism. The saline within the cooling catheter is circulated at 5 cc/sec. The saline travels through the heat exchanger in the chilled water bath and is cooled to approximately 1° C.
15. It subsequently enters the cooling catheter where it is delivered to the heat transfer element. The saline is warmed to approximately 5–7° C. as it travels along the inner lumen of the catheter shaft to the end of the heat transfer element.

16. The saline then flows back through the heat transfer element in contact with the inner metallic surface. The saline is further warmed in the heat transfer element to 12–15° C, and in the process, heat is absorbed from the blood, cooling the blood to 30° C. to 32° C.
17. The chilled blood then goes on to chill the brain. It is estimated that 15–30 minutes will be required to cool the brain to 30 to 32° C.
18. The warmed saline travels back down the outer lumen of the catheter shaft and back to the chilled water bath where it is cooled to 1° C.
19. The pressure drops along the length of the circuit are estimated to be 2–3 atmospheres.
20. The cooling can be adjusted by increasing or decreasing the flow rate of the saline. Monitoring of the temperature drop of the saline along the heat transfer element will allow the flow to be adjusted to maintain the desired cooling effect.
21. The catheter is left in place to provide cooling for 12 to 24 hours.
22. If desired, warm saline can be circulated to promote warming of the brain at the end of the therapeutic cooling period.

Figure 11:
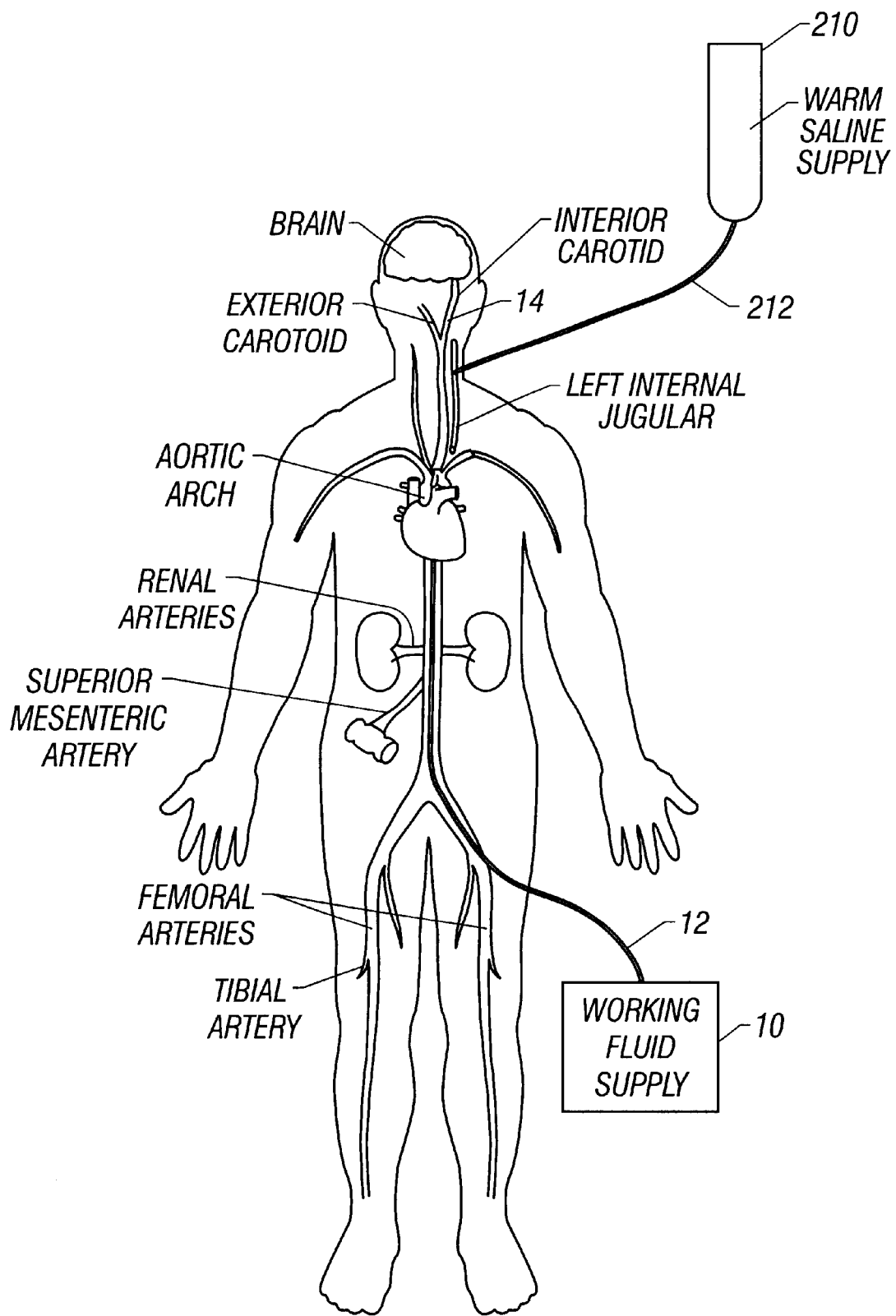
FIG. 11 is a schematic representation of the heat transfer element being used in one embodiment to cool the brain of a patient, while a warm saline solution is infused to warm the blood returning from the brain in the jugular vein.
Figure 12:
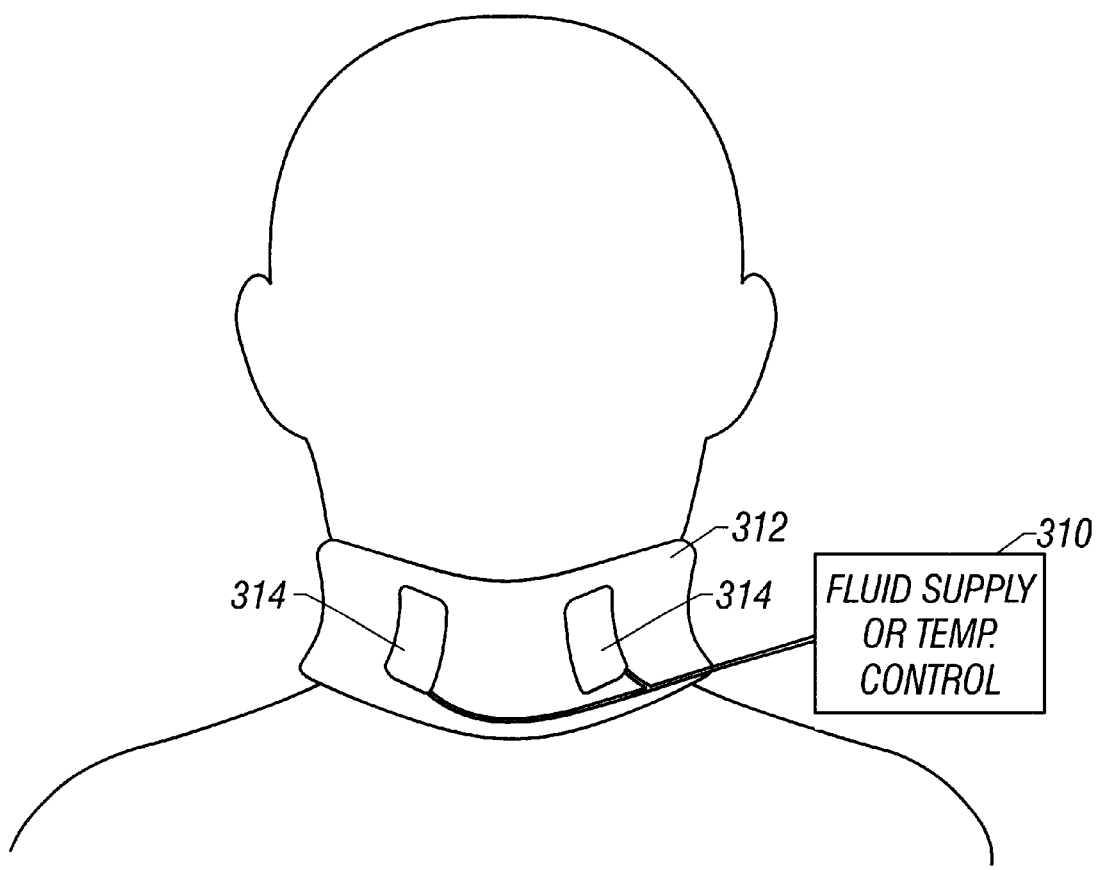
FIG. 12 is a schematic representation of one embodiment of an external warming device which can be used to warm the blood returning from an organ in a vein.

Percutaneous placement of the warming element 114 into the jugular vein is accomplished directly, since the jugular vein is close to the surface. The catheter would reside in the internal jugular and into the superior vena cava or even the right atrium. Jugular venous catheters are known. As an alternative to warming of the blood in the jugular vein with a warming element 114, a warm saline solution can be infused into the jugular vein from a saline supply 210, via an intravenous catheter 212, as shown in FIG. 11. This is advantageous since saline drips are often necessary anyway as maintenance fluids (1000 to 2500 cc/day). As yet another alternative, warming can be applied externally to the patient. The means of warming can be a heating blanket applied to the whole body, or localized heating of veins returning from the organ being cooled. As an example, FIG. 12 shows a neck brace 312 being used to immobilize the head of the patient. Immobilization of the head can be necessary to prevent movement of the cooling element, or to prevent puncture of the feeding artery by the cooling element. The neck brace 312 can have one or more warming elements 314 placed directly over the left and right internal jugular veins, to heat the blood flowing in the jugular veins, through the skin. The warming elements 314 can be warmed by circulating fluid, or they can be electrical resistance heaters. Temperature control can be maintained by a working fluid supply or controller 310.

While the invention herein disclosed is capable of obtaining the objects hereinbefore stated, it is to be understood that this disclosure is merely illustrative of the presently preferred embodiments of the invention and that no limitations are intended other than as described in the appended claims.

I claim:

1. A selective organ cooling system, comprising:
   a flexible catheter insertable into an artery feeding the brain of a patient;
   a cooling element attached to a distal end of said catheter; and
   a collar adapted for application to the neck of the patient, said collar being adapted to apply heat only to the area of the neck over the jugular veins to maintain the temperature of the remainder of the patient's body, exclusive of the brain.

2. The system recited in claim 1, further comprising a source of energy connected to said collar to generate heat for application only to the jugular vein area of the neck of the patient via said collar.

3. The system recited in claim 2, further comprising a control device adapted to regulate the application of heat only to the jugular vein area of the neck of the patient.

4. The system recited in claim 3, wherein said source of energy comprises an electrical circuit connected to a resistance heater in only the portion of said collar adapted to contact the jugular vein area of the neck of the patient.

5. A selective organ cooling system, comprising:
   a flexible catheter insertable into an artery feeding the brain of a patient;
   a cooling element attached to a distal end of said catheter; and
   a collar adapted for application to the neck of the patient, to apply heat to maintain the temperature of the remainder of the patient's body, exclusive of the brain;
   a source of energy connected to said collar to generate heat for application to the neck of the patient only via conduction from said collar; and
   a control device adapted to regulate said application of conductive heat to the neck of the patient;
   wherein said source of energy comprises a supply of warm circulating fluid connected to circulate warm fluid through a fluid tight heat exchanger in said collar.

6. The system recited in claim 5, wherein said control device is adapted to regulate said application of only conductive heat by regulating the flow rate of said warm fluid circulating through said fluid tight heat exchanger.

7. The system recited in claim 5, wherein said control device is adapted to regulate said application of only conductive heat by regulating the temperature of said warm fluid circulating through said fluid tight heat exchanger.

8. A selective organ cooling system, comprising:
   a flexible catheter insertable into an artery feeding the brain of a patient;
   a cooling element attached to a distal end of said catheter; and
   a collar adapted for application to the neck of the patient, said collar being adapted to apply heat only via conduction and only to the area of the neck over the jugular veins to maintain the temperature of the remainder of the patient's body, exclusive of the brain;
   a supply of warm circulating fluid connected to circulate warm fluid through a fluid tight heat exchanger in only the portion of said collar adapted to contact the jugular vein area of the neck of the patient, to apply heat only to the jugular vein area of the neck of the patient; and
   a control device adapted to regulate said application of only conductive heat, only to the jugular vein area of the neck of the patient.

9. The system recited in claim 8, wherein said control device is adapted to regulate said application of only conductive heat by regulating the flow rate of said fluid circulating through said fluid tight heat exchanger.

10. The system recited in claim 8, wherein said control device is adapted to regulate said application of only conductive heat by regulating the temperature of said fluid circulating through said fluid tight heat exchanger.

* * * * *